United States Patent
Lee et al.

(10) Patent No.: US 6,323,297 B1
(45) Date of Patent: Nov. 27, 2001

(54) LOW DIELECTRIC CONSTANT MATERIALS WITH IMPROVED THERMAL AND MECHANICAL PROPERTIES

(75) Inventors: Chung J. Lee; Hui Wang, both of Fremont; Giovanni Antonio Foggiato, Morgan Hill, all of CA (US)

(73) Assignee: Quester Technology, Inc., Fremont, CA (US)

( * ) Notice: Subject to any disclaimer, the term of this patent is extended or adjusted under 35 U.S.C. 154(b) by 0 days.

(21) Appl. No.: 08/958,057

(22) Filed: Oct. 24, 1997

(51) Int. Cl.[7] .................................................. C08F 14/18
(52) U.S. Cl. ..................... 526/251; 526/242; 526/250; 526/253; 427/235.6; 427/255.1; 427/255.2; 427/248.1

(58) Field of Search .............................. 427/255.6, 255.1, 427/255.2, 248.1; 526/242, 250, 251, 253

(56) References Cited

FOREIGN PATENT DOCUMENTS

WO 97/15951 * 5/1997 (WO).

* cited by examiner

*Primary Examiner*—David W. Wu
*Assistant Examiner*—Ling-Siu Choi
(74) *Attorney, Agent, or Firm*—Fliesler, Dubb, Meyer & Lovejoy

(57) ABSTRACT

New starting materials and methods are used to make materials with low dielectric constant through the processes of transport polymerization or chemical vapor deposition. The starting materials and precursors are designed to provide polymers with combined low dielectric constant, high thermal stability and high mechanical strength.

22 Claims, 28 Drawing Sheets

&

↑

1,2 (IV)

PTFE

PPP

| K | Td (°C/N$_2$) | Tg (°C) | E (Gpa) | G (Gpa) |
|---|---|---|---|---|
| 2.34 | 540 | 172 | 3.41 | 0.35 |
| 2.10 | 550 | 301 | 4.80 | 0.42 |
| 2.42 | 550 | 200 | 4.73 | 0.50 |
| 2.20 | 560 | 346 | 6.35 | 0.57 |
| 2.40 | 545 | 211 | 3.52 | 0.34 |
| 2.25 | 555 | 300 | 4.30 | 0.38 |
| 2.15 | 565 | 394 | 5.25 | 0.42 |

FIG. - 28

LOW DIELECTRIC CONSTANT MATERIALS WITH IMPROVED THERMAL AND MECHANICAL PROPERTIES

CROSS REFERENCE

Lee et al., Precursors for Making Low Dielectric Constant Materials with Improved Thermal Stability, U.S. Pat. No. 6,020,458, issued Feb. 1, 2000.

Lee et al. Chemicals and Processes for Making Fluorinated Poly(Para-Xlylenes), U.S. Pat. No. 6,140,456, issued Oct. 31, 2000.

Lee et al., New Deposition Systems and Processes for Transport Polymerization and Chemical Vapor Deposition, U.S. Pat. No. 6,086,679, issued Jul. 11, 2000.

Lee et al., Low Dielectric Constant Materials Prepared from Photon or Plasma Assisted Chemical Vapor Deposition and Transport Polymerization of Selected Compounds, U.S. Pat. No. 6,051,321, issued Apr. 18, 2000.

All of the above co-pending applications are herein incorporated fully by reference.

FIELD OF THE INVENTION

This invention reveals new starting chemical compositions and processes that are useful for making thin film polymers through the process of transport polymerization and chemical vapor deposition. The products prepared from this invention have a low dielectric constant, K, good thermal stability and have improved mechanical properties. The low K products are useful as intermetal dielectric and interlevel dielectric materials for future fabrication of integrated circuits.

BACKGROUND OF THE INVENTION

For the past 20 years, the integrated circuit (IC) device density has doubled about every 18 months. When the gate length of integrated circuits is less than 0.18 $\mu$m, the propagation time or delay time is dominated by interconnect delay instead of device gate delay. To address this problem, new materials with low dielectric constants are being developed. The aim of this development is to decrease time constant (RC delay), decrease power consumption, and decrease cross-talk in integrated circuits. There are two groups of low K dielectric materials, the traditional inorganic group exemplified by $SiO_2$, and newer organic polymers, exemplified by poly(para-xylylene). Organic polymers are considered an improvement over inorganic low dielectric materials because the K of organic polmers can be as low as 2.0. However, most of the currently available organic polymers have serious problems. Specifically, they have insufficient thermal stability, and are difficult and expensive to manufacture in a vacuum system.

For IC features of 0.35 $\mu$m, current production lines use materials consisting primarily of $SiO_2$. The $SiO_2$ products have dielectric constants ranging from 4.0 to 4.5. In addition, stable fluorinated $SiO_2$ materials with a dielectric constant of 3.5 have been achieved. These $F—SiO_2$-containing materials are primarily obtained from plasma enhanced chemical vapor deposition (PECVD). and high density, plasma chemical vapor deposition (HDPCVD) of various siloxane containing compounds such as trimethylsiloxane (TMS), tetraethylorthosilicate (TEOS) and silazanes in conjunction with $SiF_4$, $C_2F_4$.

1. Precursors and Polymers

Several thermally stable polymers or polymer precursors arc under study. These include polyimides (PIM), fluorinated polyimides (F-PIM). polyquinoxalines (PQXL), benzocyclobutenes (BCB), fluorinated polyphenylethers (F-PPE), and several types of silsesquisiloxanes. These polymers have dielectric constants ranging from 2.6 to 3.0. Solutions of these polymers or their precursors are used in spin coating processes to achieve gap filling and planarization over metal features. However, the dielectric constants of these polymers is too high for the future ICs faith small feature sizes. In addition, all thermally stable polymers including PIM and PQXL have a persistent chain length (PCL; or the loop length of a naturally curling up polymer chain) up to several hundred or thousands of Å. Long PCL makes complete gap filling very difficult if not physically impossible.

Recently, another type of low dielectric material, poly(para-xylylene) (PPX) has been studied and evaluated for future IC fabrication. These PPX include Parylene-N™, Parylene-C™ & Parylene-D™ (trademarks of Special Coating System Inc.'s poly(para-xylylenes). Currently, all commercially available poly(para-xylylenes) are prepared from dimers. The currently available starting materials or dimers for manufacturing poly(para-xylytenes) arc expensive (>$500 to $700/kg). Unfortunately, these poly(para-xylylenes) have high dielectric constants (K=2.7–3.5) and low thermal stability (decomposition temperature, Td is <320° C.–350° C. in vacuum), and thus are not suitable for IC fabrication requiring high temperature processing.

The fluorinated poly(para-xylylene) (F-PPX) or Parylene AF-4™, for example, has the structure of $(—CF_2—C_6H_4—CF_2—)_n$. It has a dielectric constant of 2.34 and is thermally stable (0.8%/hr. wt. loss at 450° C. over 3 hours in nitrogen atmosphere).

II. Processes for Manufacturing Polymers

Currently fluorinated poly (para-xylylenes) are polymerized from F-dimers by the method of Gorham, (*J. Polymer Sci.* A1(4):3027 (1966)) as depicted in Reaction 1 below:

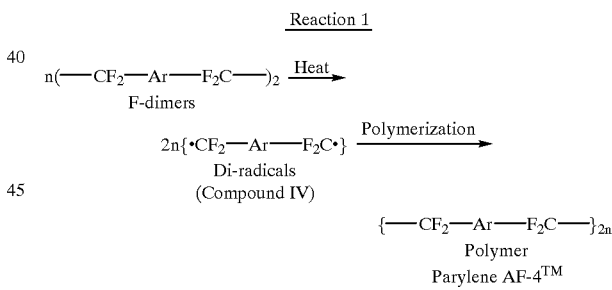

In this reaction Ar is $—C_6H_4—$. However, the precursor molecule and the F-dimer needed for the manufacture of Parylene AF-4™ is expensive and time-consuming to make because several chemical reaction steps are needed to make its fluorinated dimer.

Fluorinated dimers are manufactured according to the following series of chemical steps:

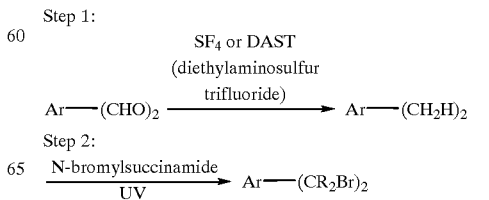

-continued

Step 3:
Ar—(CR$_2$Br)$_2$ ⟶ Ar—(CF$_2$—NR$_3$)$_2$

Step 4a:
Ar—(CR$_2$Br)$_2$ $\xrightarrow{\text{Ag}_2\text{O/tetrahydrofuran}}$ F-dimer or Step 4b:
Ar—(CF$_2$—NR$_3$)$_2$ $\xrightarrow{\text{Hoffman Elimination}}$ F-dimer The overall yields for making F-dimers is low (estimated from 12% to 20% based on the weight of its starting material). In addition, the last step of the syntheses of the precursor. or the dimerization step (4a or 4b), can only be effectively carried out in very dilute solutions (from 2% to less than 10% weight/volume) resulting in low conversion efficiecy. Further, the needed lead time and material cost for making F-containing dimers is very high. For instance, 10 g of the F-dimer can cost as much as $2,000/g. The lead time is 2–3 months for getting 1 kg of sample from current pilot plant production facilities.

Therefore, even though fluorinated poly(para-xylylenes) might be suitable as dielectric materials in "embedded" IC structures, it is very unlikely that the F-dimer will ever be produced in large enough quantity for cost effective applications in future IC fabrication.

On the other hand, a readily available di-aldehyde starting material (Compound Ia) is reacted with sulfurtetrafluoride at an elevated pressure of 1 MPa to 20 MPa and temperatures of 140° C. to 200° C. to yield the tetrafluorinated precursor (Compound IIIa) and sulfur dioxide (Reaction 2). The sulfur dioxide is then exhausted from the reaction chamber. Alternatively, the di-aldehyde can be reacted with diethylaminosulfur trifluoride (DAST) at 25° C. at atmospheric pressure to make the Compound IIIa.

Reaction 2

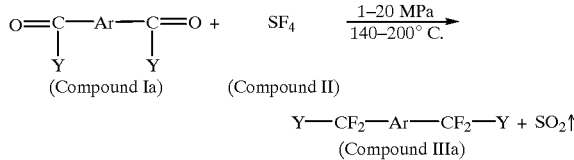

Y is H, and Ar is phenylene moiety. Both Compound Ia and Compound IIIa have a non-fluorinated phenylene moiety. The Compound IIIa in solution can be converted into a dibromo Compound IIIb (see below, Reaction 3) through a photo-reaction (Hasek et al., *J. Am. Chem. Soc.* 82:543 (1960). The dibromo Compound IIIb (1–5%) was used in conjunction with CF$_3$—C$_6$H$_4$—CF$_3$ by You, et al., U.S. Pat. No. 5,268,202 to generate di-radicals (Compound IV) that was transported under low pressure to a deposition chamber to make thin films of fluorinated poly(para-xylylenes).

Reaction 3

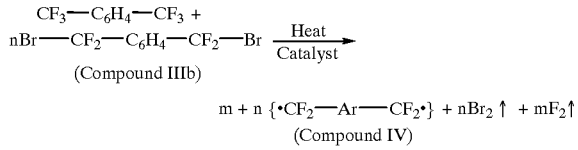

Additionally, poly(para-xylylene)-N (Parylene-N™ or PPX-N) was also prepared directly from pyrolysis of p-xylene. (Errede and Szarwe, *Quarterly Rev. Chem. Soc.* 12:301 (1958); Reaction 4). According to this publication, highly cross-linked PPX-N was obtained.

Reaction 4

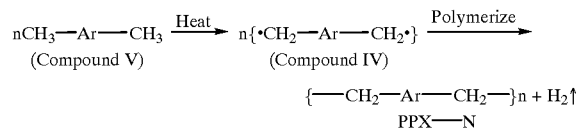

III. Deposition of Polymer Films

The deposition of low dielectric materials onto wafer surfaces has been performed using spin on glass (SOG), but for newer devices which have features smaller than 0.25 µm, SOG processes cannot fill the small gaps between features. Therefore, vapor deposition methods are preferred. Of these, transport polymerization (TP) and chemical vapor deposition (CVD) are most suitable.

In both TP and CVD, the precursor molecule is split (cracked) to yield a reactive radical intermediate which upon deposition onto the wafer can bind with other reactive intermediate molecules to form a polymer. The polymer thus forms a thin film of material with a low dielectric constant.

Chemical vapor deposition has been used to deposit thin films with low dielectric constant. Sharangpani and Singh, *Proc. 3d Int. DUMIC Conference.* 117–120 (1997) reported deposition of amorphous poly(tetrafluoroethylene) (PFTE; Teflon™, a registered trade name of DuPont, Inc.) by a direct liquid injection system. A solution of PFTE is sprayed on a wafer substrate, which is exposed to ultraviolet light or light from tungsten halogen lamps. Unfortunately, PFTE has a low glass transition temperature (Tg) and cannot be used for IC fabrication requiring temperatures of greater than 400° C.

Labelle et al., *Proc. 3d Int. DUMIC Conference*, 98–105 (1997) reported using pulsed radio frequency (RF) plasma enhanced CVD (PECVD) process for deposition of hexafluoropropylene oxide. However, as with poly (tetrafluoroethylene), the resulting polymers have low Tg values and cannot be used as dielectrics.

Kudo et al., *Proc. 3d Int. DUMIC Conference*, 85–92 (1997) reported using a PECVD process for deposition of hydrocarbons including C$_2$H$_2$/(C$_2$H$_2$+C$_4$F$_4$).

Lang et al., *Mat. Res. Soc. Symp. Proc.* 38 1:45–50 (1995) reported thermal CVD process for deposition of poly (naphthalene) and poly(fluorinated Naphthalene). Although polymers made from these materials have low dielectric constants, the polymers are very rigid, being composed of adjoining naphthalene moieties. Thus, they are prone to shattering with subsequent processing such as Chemical Mechanical Planarization (CMP).

Selbrede and Zucker, *Proc. 3d Int. DUMIC Conference*, 121–124 (1997) reported using a thermal TP process for deposition of Parylene-N™. The dielectric constant of the resulting polymer (K=2.65–2.70) also was not low enough. For future IC applications, the decomposition temperature (Td) of the thin film was also too low to withstand temperatures greater than 400° C.

Wang et al., *Proc. 3d Int. DUMIC Conference*, 125–128 (1997) reported that annealing a deposited layer of poly (para-xylylene) increases the thermal stability, but even then, the loss of polymer was too great to be useful for future IC manufacturing.

Wary et al. (*Semiconductor International, June* 1996. pp: 211–216) used a fluorinated dimer. the cyclo-precursor (α, α,α',α', tetrafluoro-di-p-xylylene) and a thermal TP process for making polmers of the structural formula: {—$CF_2$—$C_6H_4$—$CF_2$—$\}_n$. Films made from Parylene AF-4™ have dielectric constant of 2.28 and have increased thermal stability compared to the hydrocarbon dielectric materials mentioned above. Under nitrogen atmosphere, a polymer made of Parylene AF-4™ lost only 0.8 % of its weight over 3 hours at 450° C.

In contrast to a CVD process, transport polymerization (TP) (Lee, C. J., Transport Polymerization of Gaseous Intermediates and Polymer Crystal Growth. *J Macromol. Sci. -Rev. Macromol. Chem.* C16:79–127 (1977–1978), avoids several problems by cracking the precursor in one chamber and then transporting the intermediate molecules into a different deposition chamber. By doing this, the wafer can be kept cool, so that deposited materials on the wafer are not disrupted, and multiple layers of interconnect devices may be manufactured on the same wafer. Further, the conditions of cracking can be adjusted to maximize the cracking of the precursor, ensuring that very little or no precursor is transported to the deposition chamber. Moreover, the density of the transported intermediates may be kept low, to discourage re-dimerization of intermediates. Thus, the thin film of low dielectric material is more homogeneous and more highly polymerized than films deposited by CVD. These films have higher mechanical strength and can be processed with greater precision, leading to more reproducible deposition and more reproducible manufacturing of integrated circuits.

Among all currently available poly(para-xylylenes), F-PPX (—$CF_2$—$C_6H_4$—$CF_2$—$)_n$ or Parylene AF-4™ has the lowest dielectric constant and best thermal stability. This resulted from a lower polarity and higher bonding energy of C—F bond compared to those of C—H bond. So far, the F-PPX is considered to be the most promising "embedded" IMD for future 0.18 $\mu$m ICs due to its low dielectric constant (K=2.34) and high thermal stability (0.8%/hr. wt. loss at 450° C. up to 3 hours). However, to be useful as an interlevel dielectric material, a lower K (K<2.3–2.5) polymer still needs to have better thermal stability, $T_d$ and thermal mechanical strength than those of the Parylene AF-4™, as higher $T_d$, glass transition temperature $T_g$ and Elastic Modulus are needed for re-flow or annealing of aluminum or copper. In addition, higher Tg and Elastic Modulus (E) are desirable for CMP to achieve global planarization. In this invention, new chemical compositions are provided to overcome the above mentioned problems.

SUMMARY OF THE INVENTION

The present invention is directed to overcoming the disadvantages of the prior art.

Accordingly, an object of the present invention is to provide a precursor for making polymers with low dielectric constants.

A further objective is to provide a precursor for making fluorinated polymers which have improved thermal stability.

A yet further objective is to provide a precursor for making fluorinated polymers which have high elastic modulus.

An additional objective is to provide a precursor for making fluorinated polymers which have high shear modulus.

A yet additional objective is to provide a precursor for making fluorinated polymers which have high glass transition temperature.

Another objective is to provide a precursor for making polymers which can be manufactured from inexpensive starting materials.

A yet further objective is to provide a precursor for making polymers which can be manufactured with high efficiency.

A additional objective is to provide a precursor for making polymers that produce low amounts of environmental toxins.

The invention includes novel precursors for making fluorinated polymers from aromatic di-aldehydes.

The invention also includes methods for making polymers made from the precursors of the invention.

The invention also includes polymer thin films deposited on substrates.

The invention further includes integrated circuits made from polymers of the invention.

Accordingly, one aspect of the invention comprises a starting material for making fluorinated polymers comprising an aromatic di-aldehyde, wherein the resulting polymer has a low dielectric constant.

Another aspect of the invention comprises a precursor for making fluorinated polymers which can be manufactured into a polymer with a high thermal stability.

Yet another aspect of the invention comprises a precursor which can be manufactured into a polymer with sufficiently high mechanical strength to be processed during the manufacture of integrated circuits.

Another aspect of the invention comprises a precursor containing fluorinated aromatic moieties.

Yet another aspect of the invention comprises methods for making polymers for integrated circuit manufacture using novel fluorinated precursors.

A yet another aspect of the invention includes thin films made from polymers manufactured using the precursors and methods.

This invention offers products with low dielectric constants and good thermal stability for use as intermetal dielectrics (IMD) and interlevel dielectrics (ILD) for the manufacture of integrated circuits. The processes provide more efficient conversion from precursors to final polymer films than conventional methods.

Other objects, aspects and advantages of the invention can be ascertained from the review of the additional detailed disclosure, the examples, the figures and the claims.

BRIEF DESCRIPTION OF THE FIGURES

FIG. 22 depicts an embodiment of a semiconductor wafer of the invention with a thin film dielectric laner and imbedded integrated circuit features.

FIG. 27 depicts the relationship between polymer structure and dielectric constant (K) for polNmers comprising selected aromatic moieties.

FIG. 28 depicts the relationship between polymer structure and K, Td, Tg, E, and G for polymers comprising selected aromatic moieties.

DETAILED DESCRIPTION OF THE PREFERRED EMBODIMENT

Figure 1:
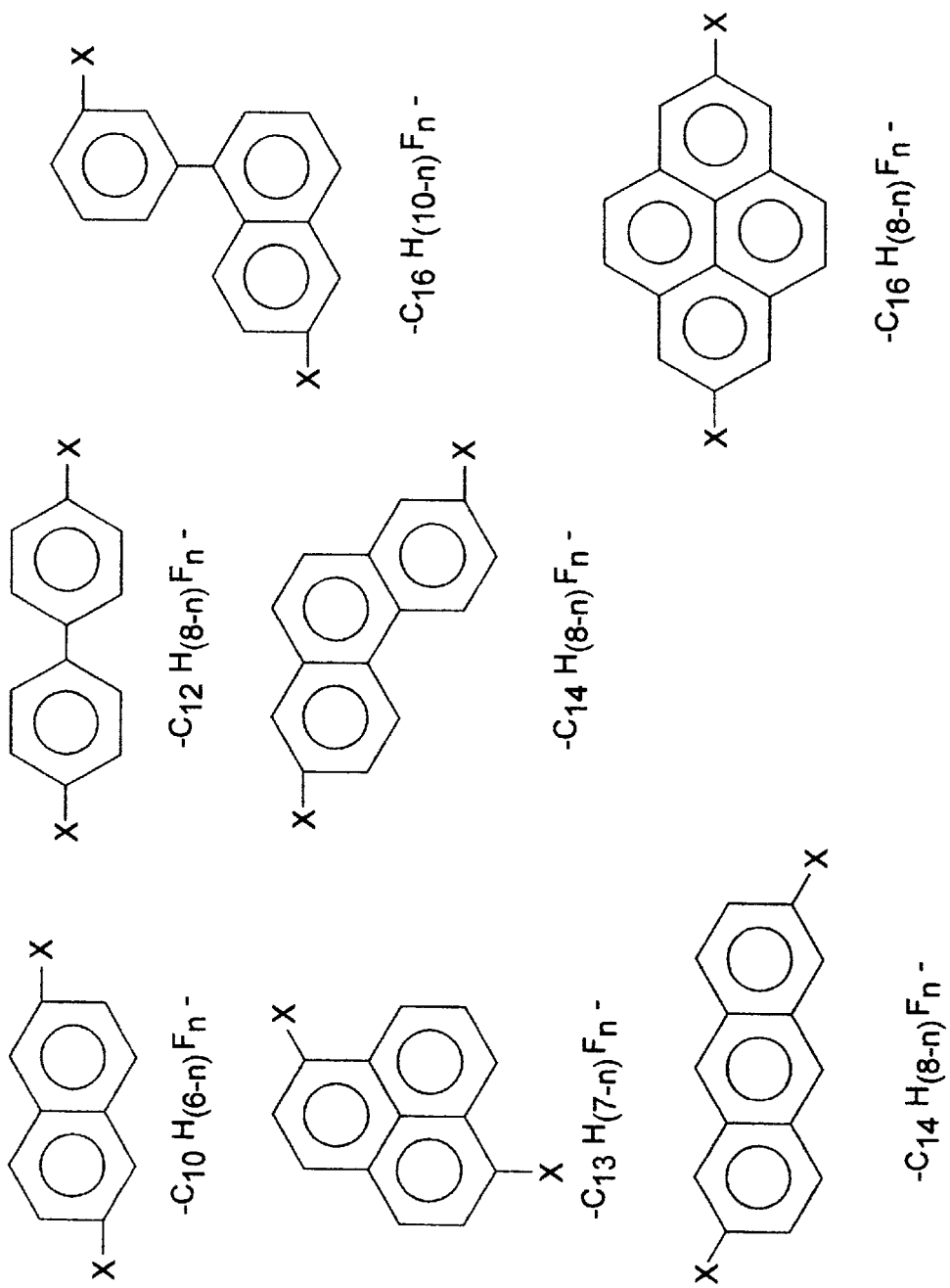
FIG. 1 depicts some of the aromatic groups of this invention.

1. Desirable Aromatic Groups For Transport Polymerization

The desirable Ar groups of this invention are designed to result in polymers that have low dielectric constants, high thermal stability and high mechanical strength. These desired properties are primarily predicted from the following publications: Lee et al., Rev. Macromol. Chem. Phys. C29 (4):431–569 (1989) and Lee et al., Polym. Eng & Sci. 27(13):1015–1017 (1987), both incorporated herein fully by reference. The specific relationships between the cohesive energy density, $\Sigma$, and Tg and elastic modulus of polymers is discussed in Bicerano, Prediction of Polymer Properties, Marcel Dekker, New York (1996), herein incorporated fully by reference). Bicerano calculated various polymer properties using some topological variables. K and $T_d$ are estimated from group contribution of known polymers according to principles taught in the reference of Lee (supra). Over twenty polmers with various aromatic (Ar) compositions in ($-CF_2-Ar-CF_2-$) were studied.

Some general design rules stated herein below have been derived for choosing starting materials that are useful for this invention. By applying these rules, it is possible to achieve materials with low dielectric constant (K<2.34) and much higher $T_g$, $T_d$, E and G than Parlene AF-4.

A. Prediction of Dielectric Constant

The dielectric constant, K is calculated using group contributions, $k_i$ derived from known polymers such as polyethylene ($-CH_2-CH_2-$), Teflon™ ($-CF_2-CF_2-$)$_n$, poly(para-xylylene N) ($-C_6H_4-CH_2-CH_2-$)$_n$, and poly(para-xylylene-F) ($-C_6H_4-CF_2-CF_2-$)$_n$, where n is an integer. From calculations of group contributions, when fluorine atoms replace hydrogen atoms in sp$^3$C—H and sp$^2$C—H groups, the decrease in K per added fluorine atom are –0.05 an –0.07, respectively. Therefore, starting materials and precursors of this invention contain more sp$^2$C—F bonds than previous materials, and thus, will decrease K.

B. Prediction of Decomposition Temperature

Decomposition temperature, Td is defined as the onset temperature of polymer decomposition when measured under 3° C./minute heating rate in a thermogravimetric analyzer under nitrogen atmosphere. Known group contributions are taken from Elhers, Structure-Stability relationships of polymers based on thermogravimetric analysis data, AFML-TR-74-177, Part 1, 1974. Td increases 15° C. for each additional sp$^2$C—F group. Td increases by 32.5° C. for each sp$^3$C—F group, by 15° C. for every sp$^2$C—F group, and by 26° C. for each sp$^2$C-sp$^3$C—F group.

C. Prediction of Glass Transition Temperature

The glass transition temperature ($T_g$) is calculated using an extended quasilattice theory according to previous methods (C. J. Lee, Polyimides, Polyquinolines and Polyquinoxalines: Tg-Structure Relationships. Rev. Macromol. Chem. Phys.C29(4):431–560 (1999). herein incorporated fully by reference). The overall accuracy of the calculations of Tg is within ±5° C. of the actually observed Tg for polymers. Tg increases by 32° C. for each additional sp$^2$C—F group, and by 33.4° C. for each sp$^3$C—F group. The increased Td and Tg arc due from increased cohesive energy (2.3 kcal/mol-F), but decreased change in heat capacity at Tg (heat capacity jump) of –0.55 Joule/mole-K.

D. Prediction of Elastic Modulus and Shear Modulus

Elastic modulus, E and shear modulus, G are calculated using a topological approach according to Bicerano (Prediction of Polymer Properties, Marcel Dekker, New York (1996), herein incorporated fully by reference). E increased by about 0.22 GPa per sp$^2$C—H group, by about 0.32 GPa per sp$^3$C—F group, and by about 0.33 GPa for each sp$^2$C—F group.

Addition of phenylene aromatic moieties ($-C_6H_4-$) increases E by 1.36 GPa per phenylene moiety, but also increases K by about 0.4 per moiety. Therefore, to increase thermal stability and decrease K, it is important to fluorinate the aromatic moieties.

The above methods used to predict physical properties of polymers are verified by experiment. The predicted and measured Tgs for polyethylene are 197° K and 195° K, respectively, and the predicted and measured Tgs for poly (xylylene) are 332° K and 333° K, respectively. The calculated and measured elastic moduli for poly(para-xylylene-N) are 2.14 and 2.4 GPa, respectively.

For the manufacture of linear polymers, it is desirable to use precursors which contain only two groups capable of forming radical intermediates. In this way, the end-to-end polymerization results in long polymer chains (over 20 repeating units). During deposition, these long polymer chains align with each other, and with the aromatic structures of adjacent polymers adjacent to each other. When polymerized, these adjacent aromatic structures can interact with each other by their $\pi$ bonds, thus increasing the strength of the polymer film, the strength being reflected in increased Td, Tg, E and G.

The aromatic groups of this invention comprises more than 6 carbon atoms, preferably a fluorine-containing aromatic radical comprising $sp^2C$—$C$ and $sp^2C$—$F$ bonds. The ratio, $\gamma$, of the $sp^2C$—$F$ bonds to $sp^3C$—$F$ bonds of the resulting polymers can be zero, but it is desirable for $\gamma$ to be more than 0.25 within the aromatic ring. For example, $\gamma$ is 0 in the polymer $(-CF_2-C_6H_4-CF_2-)_n$ and is 0.25 in the polymer $(-CF_2-C_6H_3F_1-CF_2-)_n$.

Polmers with higher $\gamma$ have higher thermal stability and lower dielectric constant due to their higher fluorine content (G. F. L. Elhers, Structure-Stability Relationships of Polymers Based on Thermogravemetric Analysis Data: Technical report Part I & II, AFML-Tr-74-177 (1974), herein incorporated fully by reference).

If the cohesive energy density, $\Sigma$, of a fluorine-containing aromatic group is higher than that of a ($-C_6H_4-$) group, the resulting polymer will have higher Td, Tg, and mechanical strength than those of Parylene AF-4™, which incorporates a non-fluorinated phenylene moiety. Polymers whose aromatic groups consist of more than 6 carbon atoms have higher Tg, higher Td and higher E than polymers whose aromatic groups consist of only 6 carbon atoms.

E. New Aromatic Moieties

New starting materials and precursors of this invention contain aromatic moieties which have greater than 6 to about 40 carbon atoms. Precursors of this invention can be classified according to the following formulas:

$-C_{10}H_{(6-n)}F_n-$, wherein n is an integer ranging from 0 to 6;

$-C_{12}H_{(8-n)}F_n-$, wherein n is an integer ranging from 0 to 8;

$-C_{13}H_{(7-n)}F_n-$, wherein n is an integer ranging from 0 to 7;

$-C_{14}H_{(8-n)}F_n-$, wherein n is an integer ranging from 0 to 8, $-C_{16}H_{(10-n)}F_n-$, wherein n is an integer ranging from 0 to 10.

Examples of precursors comprising aromatic groups of this invention are shown in FIG. 1. The aromatic groups include the di-phenylenyl moiety ($-C_{12}H_{(8-n)}F_n$), where n is an integer of from 0 to 8, consists of two phenylenyl moieties covalently linked together. The anthracenyl ($-C_{14}H_{(8-n)}F_n-$) moiety, wherein n is an integer of from 0 to 6, the phenanthrenyl ($-C_{14}H_{(8-n)}F_n-$) moiety, wherein n is an integer of from 0 to 8, the 4-ring pyreneyl ($-C_{16}H_{(8-n)}F_n-$) moiety, wherein n is an integer of from 0 to 8, are useful. Further, more complex aromatic structures such as a naphthenyl moiety connected to a phenylene moiety ($-C_{16}H_{(10-n)}F_n-$), wherein n is an integer from 0 to 10, are useful in this invention. Furthermore, a three-ring structure ($-C_{13}H_{(7-n)}F_n-$) also is useful.

Moreover, covalently linking similar or different aromatic residues together creates larger aromatic moieties. For example, linking phenyleneyl and naphthenyl residues into a phenyleneyl-naphthenyl moiety results in an aromatic moiety with the structural formula: $(C_6H_{4-n}F_n)-(C_{10}H_{6-m}F_m)$, where n and m are integers. Similarly, linking a phenanthrenyl residue and a pyreneyl residue results in an aromatic moiety with the structural formula: $-(C_{14}H_{(8-n)}F_n)-(C_{16}H_{(8-n)}F_n)-$. All such combinations of the aforementioned aromatic moieties which consist of up to about 40 carbon atoms are considered to be part of this invention.

The reactive groups (X) attached to aromatic moieties useful for polymerization of precursors of this invention are $-CF_2Y$, wherein Y is a leaving group selected from the group consisting of $-H$, $-Cl$, $-Br$, $-NR$, $-SR$, $-SiR_3$, $-NR_2$ and $-SO_2R$ and wherein R is $-H$, an alky group or an aromatic mono-radical.

Figure 2:
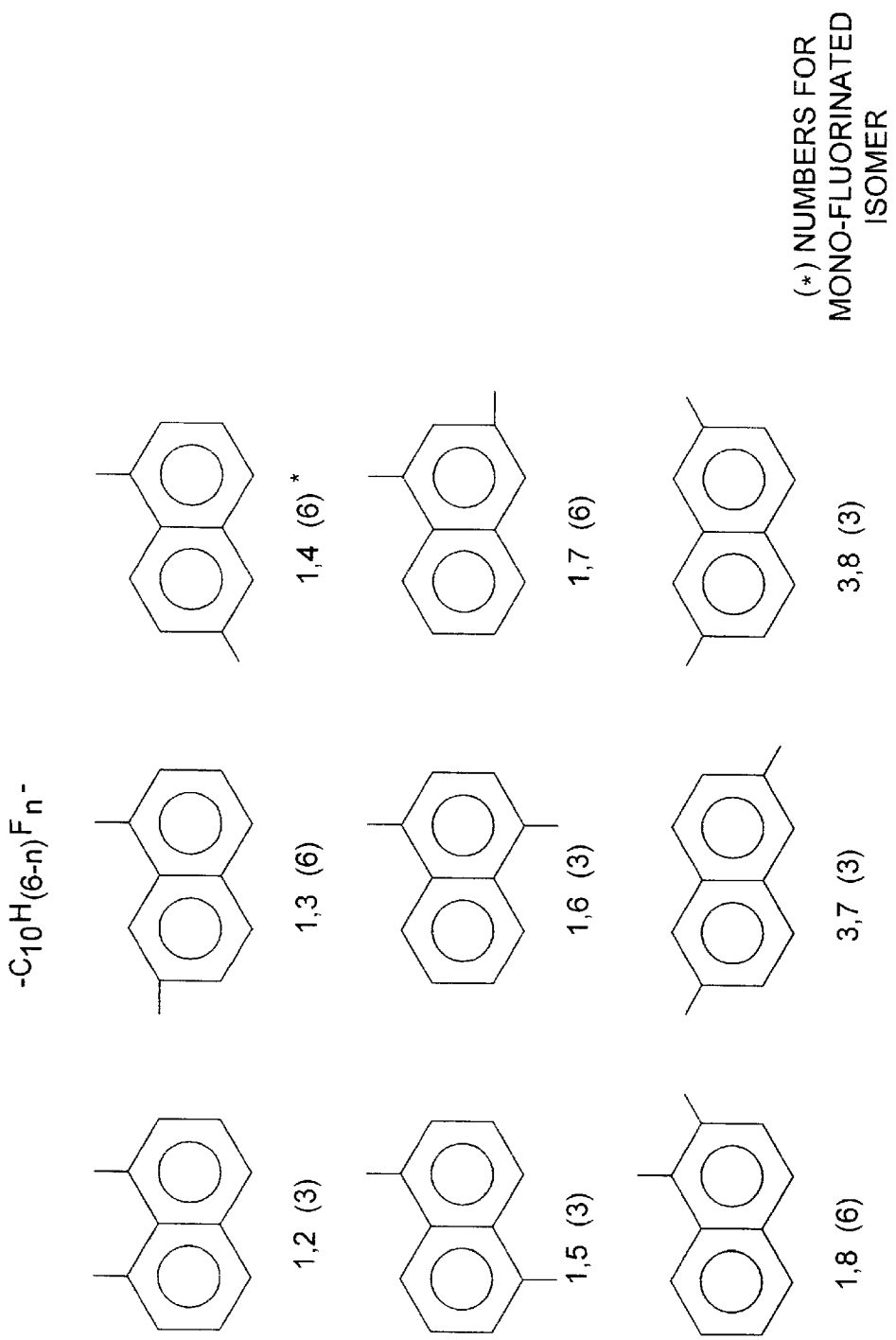
FIG. 2 depicts several bi-functional isomers of naphthalenyl moieties (—$C_{10}H_{(6-n)}F_n$—) of this invention.

Numerous positional isomers exist for each of the above formulas. The term positional isomer refers to the relative location of the radical-containing moieties on the aromatic groups. In addition to positional isomers, the location of the fluorine atoms also may be different for each of the positional isomers. For instance, when the aromatic group has the general formula: $-C_{10}H_{(6-n)}F_n-$, there are 9 and 39 positional isomers for n=0 and 1 respectively (see FIG. 2), For each of the positional isomers shown in FIG. 2, there are several fluorine-isomers. The number of these mono-fluoro-isomers is shown in parentheses. All partially or fully fluorinated aromatic moieties and all of the positional isomers are included in this invention.

However, not all of these positional isomers are equally useful in transport polymerization for the preparation of thin films for IC fabrication. Isomers, when formed into reactive intermediate di-radicals (Compound IV), may not form polymers at all. For example, in the (1,2) isomer of Compound IV (FIG. 2), the radical groups are too close together on the aromatic moiety, and the reactive intermediates will mostly form side products such as monomers and dimers (FIG. 3), and not will not form polymers. When these monomers and diners deposit on wafers along with polymers, the resulting thin films will be contaminated with liquid or powdered side products, and thereby become useless for IC fabrication. For the same reason, the (1, 8) isomer is not useful.

These powdery dimers form on wafers when the vapor pressure is too high or/and its residence time, $\tau$, inside the chamber is too long. Attempts to increase deposition rate by increasing the chamber pressure resulted in more dimer formation and resulting loss of deposition efficiency unless the residence time in the chamber is very low. The sufficiently short residence time needed to avoid powder formation on cold wafers can only be obtained by using small deposition chambers. Because the smallest chamber size is limited by the wafer diameter, the height of the chamber should be very small. Constraints on the dimensions of the chamber can lead to poor deposition patterns such as non-uniformity if the flow of intermediates is focused on a particular portion of the wafer. In some of the new deposition systems of co-pending applications, the chamber is designed to accommodate devices which can re-distribute the flow pattern of intermediates onto the wafers. If the chamber is too small, there will be insufficient room to incorporate flow pattern adjusters or diffusion plates into the systems. Moreover, with small chamber dimensions, it is difficult to provide adequate devices for automated water handling.

Figure 4:
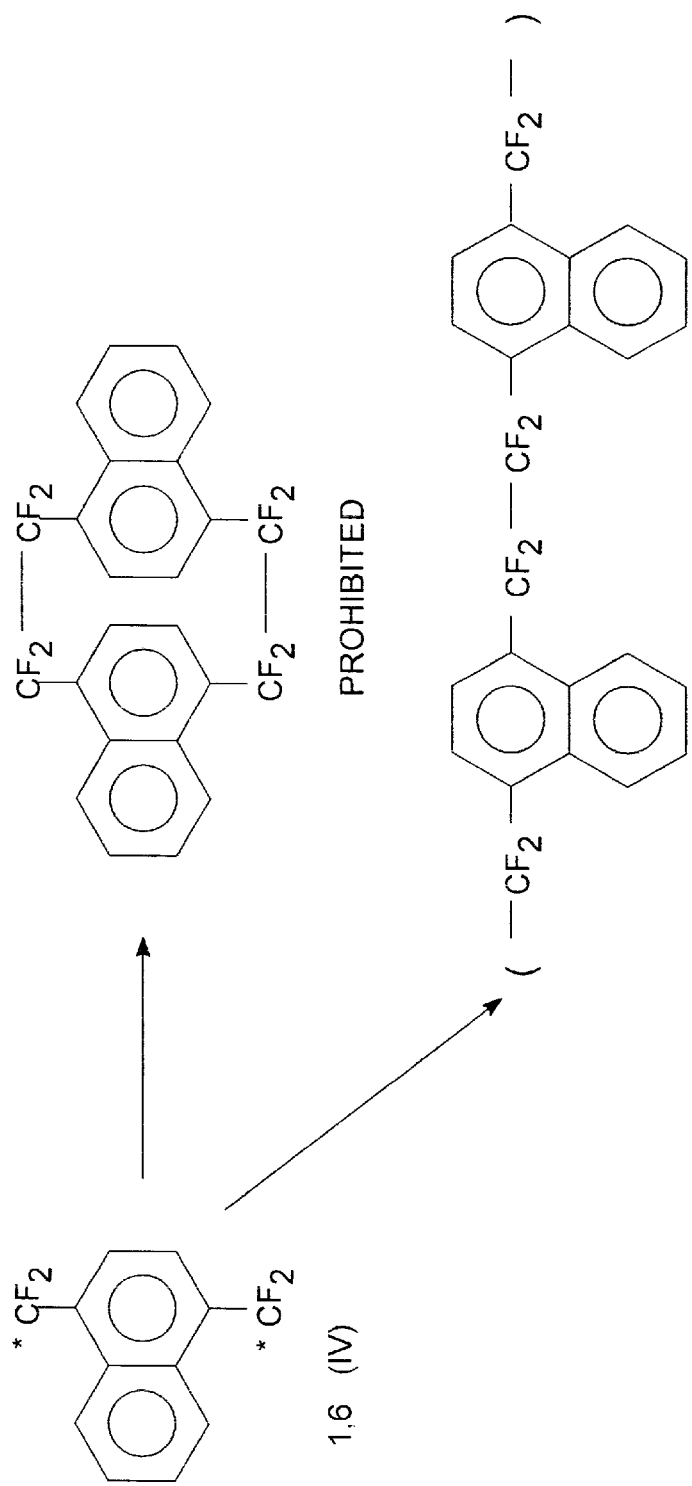
FIG. 4 depicts two potential reaction pathways of the (1,6) isomer of naphthalenyl moieties.

On the another hand, intermediate di-radicals (Compounds IV) generated from the (1,6) isomer will not form dimers because of the steric hindrance of its bulky Ar group as shown in FIG. 4. For the same reason, except for the (1,2) and (1,8) isomers, other C-10 di-radicals will tend not to form side products on wafers even though they have a high residence time and/or under high vapor pressure. These polymer precursors are favored for potentially getting much higher deposition rates.

It is desirable to chose isomers in which the formation of dimers or monomers is not favored. By selecting the positional isomers such that the reactive groups are sufficiently far apart, dimer or monomer formation is minimized. It is desirable for the end-to-end length ($I_{gu}$) to be at least 4 Å, and preferably, $I_m$ should be at least 6 Å. End-to-end length is calculated using bond angle and bond length of repeating units in the polymers.

Asymmetrical isomers with lower extended chain lengths will have higher G and E. However, symmetrical isomers have higher Tg due to the higher cohesive energy, which results from the more complete alignment of aromatic moieties. The more complete alignment results in closer approximation of π electrons in the adjacent aromatic moieties, which results in the formation of tighter π bonds being formed between adjacent aromatic moieties.

Figure 5:
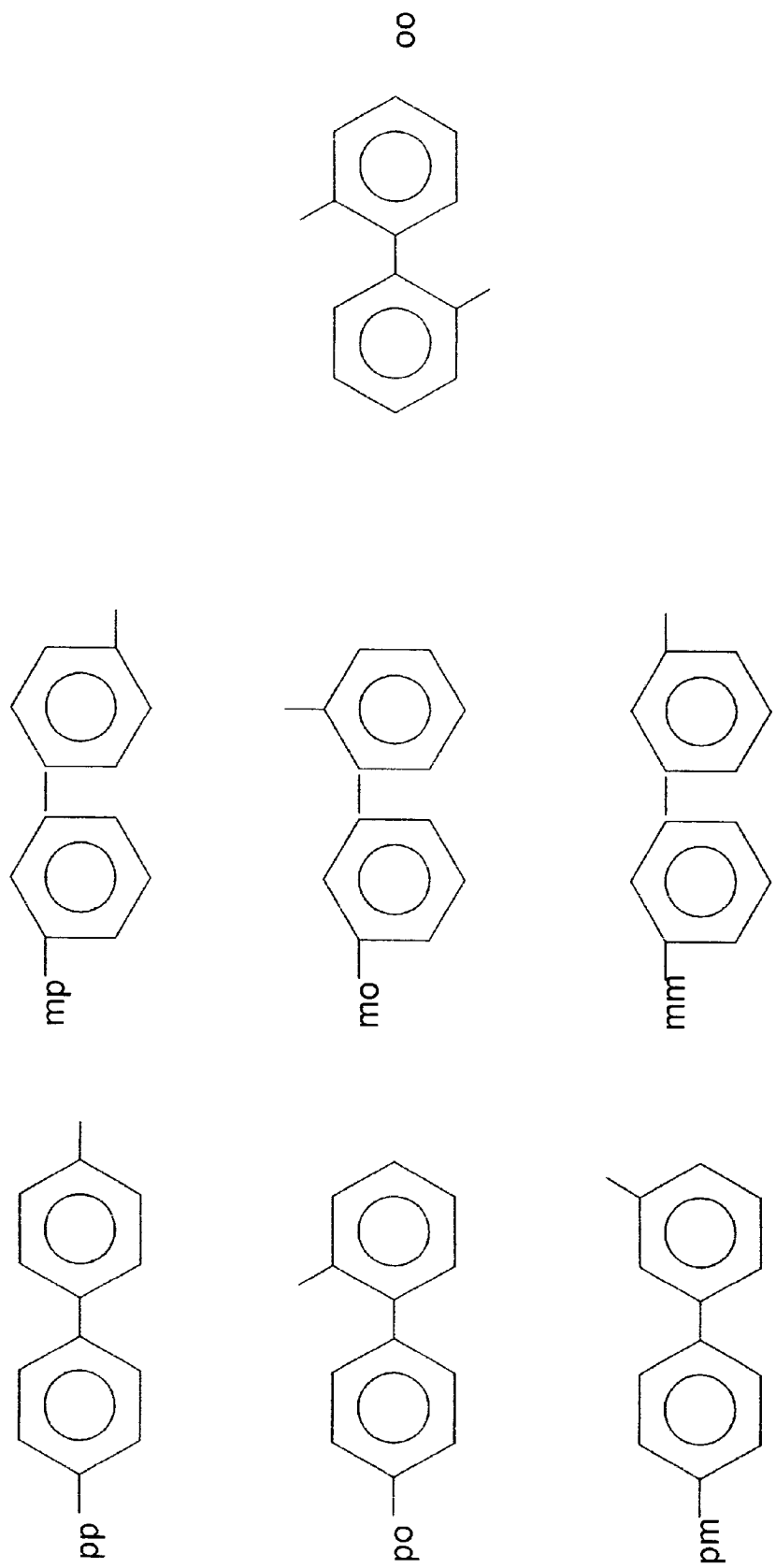
FIG. 5 depicts isomers of (—$C_{12}H_{(8-n)}F_n$—) of this invention which are useful in manufacture of polymers.

For the di-phenylene moiety, there are several positional isomers (FIG. 5). In these positional isomers, the arrangement of the reactive groups can be para-para (pp), meta-para (mp). para-ortho (po), meta-ortho (mo), ortho-ortho ("oo"), para-meta (pm). or meta-meta (mm). Note that the oo positional isomer will be constrained to a trans configuration, wherein the two radical-containing moieties of Compound IV will not be close together. If they are too close together, they may form a monomer which will contaminate the polymer. Fortunately, the "oo" monomer is highly unstable, and does not easily form.

Some of the naphthenyl ($C_{10}$) isomers, such as the (1, 5) and (3, 7) isomers, $C_{12}H_{(8-n)}F_n$, $C_{14}H_{(8-n)}F_n$, $C_{16}H_{(8-n)}F_n$ (FIG. 1) and others have a symmetric configuration, therefore they are likely to form highly crystalline polymers. For the same polymer, thin films with higher degrees of crystallinity have higher thermal stability, higher Elastic Modulus and higher $T_g$ and lower Coefficient of Thermal Expansion (CTE). For this reason, Parylene AF-4™ deposited at higher wafer temperatures resulted in higher $T_g$ and E and lower CTE than those of films deposited at lower wafer temperatures.

Figure 7:
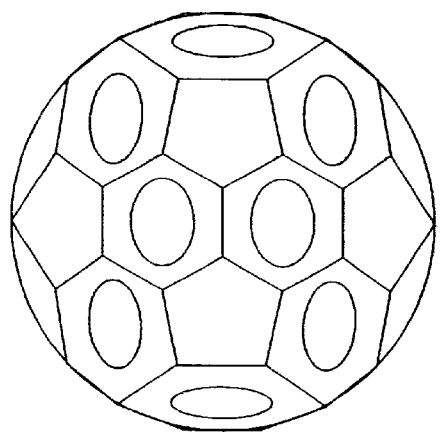
FIG. 7 depicts the co-polymerization of Buckminster fullerene with aromatic moieties of this invention.
Figure 7:

In addition to planar aromatic moieties, fullerenes also can be incorporated into polymer networks of this invention. FIG. 7 shows the reaction of Buckminster fullerene ($C_{60}$) and a fluorinated phenylenyl moiety to form a co-polymer in which the fullerene and phenylenyl moieties alternate with each other, being separated by $CF_2$—$CF_2$ groups. (See. *J. Amer. Chem. Soc.* 114:3977–3978 (1992), herein incorporated fully by reference). Fullerenes have high mechanical strength, primarily due to the presence of $sp^2C$-$sp^2C$ bonds.

II. Preparation of Precursors from Starting Materials

Reaction 5 below describes the preparation of a tetrafluoro precursor compound from sulfur tetrafluoride and a starting material (Compound Ib):

Reaction 5

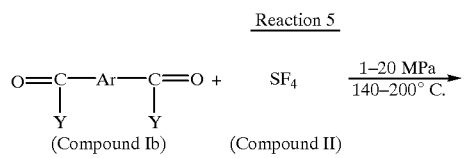

-continued

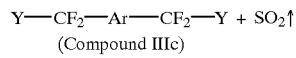

(Compound IIIc)

Compounds Ib and IIIc contain aromatic moieties of at least 6 carbon atoms containing at least one fluorine atom. In the above, Y is preferably a leaving group comprising —H. Alternatively, other precursors (Compound IIIc), where Y is —SR —Br, —Cl, —NR₃, —SO₂R, —OR, —CR₃, wherein R groups are H, alkyl or aromatic groups, can be prepared from the brominated derivatives of its tetrafluoro Compound IIIa (where Y=H). [Chow et al., *Jour. Org. Chem.* 35(1):20–21 (1970); Chow et al., U.S. Pat. No. 3,268,599; Hartner, U.S. Pat. No. 4,532,369.] These references are incorporated herein fully by reference. These precursors have lower C—Y bonding energy than C—F bonds, thus providing lower processing temperatures when thermolytic methods are employed. For manufacturing linear, weakly-cross-linked polymers, preferred Y groups are —Br, —NR₃ and —SR.

For manufacturing more highly cross-linked polymers, the preferred Y group is —H. The Ar is an aromatic moiety consisting of at least 6 carbon atoms, preferably a F-containing aromatic radical comprising $sp^2C$—F bonding. $sp^2C$—refers to a bond tyke in which a carbon atom is connected to other elements with at least one double bond such as C═C. $sp^3C$—refers to a bond type in which a carbon atom is connected to other elements with single bonds such as those in C—F₄.

III. Polymerization of Aromatic Precursors

The precursors of this invention can be deposited using any conventional and novel methods, including Chemical Vapor Deposition (CVD) and Transport Polymerization (TP). The invention comprises a (1) direct method for generation of the di-radicals (Compound IV) from the tetrafluoro Compound IIIc, (2) new precursors containing a fluorinated aromatic moiety having from 7 to 40 carbon atoms, and (3) newly designed equipment to facilitate the reactions for IC fabrication. Further description of the equipment used is found in the above-identified co-pending application titled "New Deposition Systems & Processes for Transport Polymerization", incorporated herein fully by reference.

In general, lower wafer temperature results in a higher deposition rate. Some useful properties of crystalline polymers may have to be compromised if a higher deposition rate is desirable in the case of Parylene AF-4™. The dependency of Parylene AF-4™ properties on the degrees of crystallinity or wafer temperature may decrease the yield or even reliability of integrated circuits made under non-ideal conditions. For instance, different layers of Parylene AF-4™ in ICs will be exposed to a different temperature history during IC fabrication, therefore the thin films of different layers will have different properties.

IV. Formation of Cross-Linked Polymers

Figure 6:
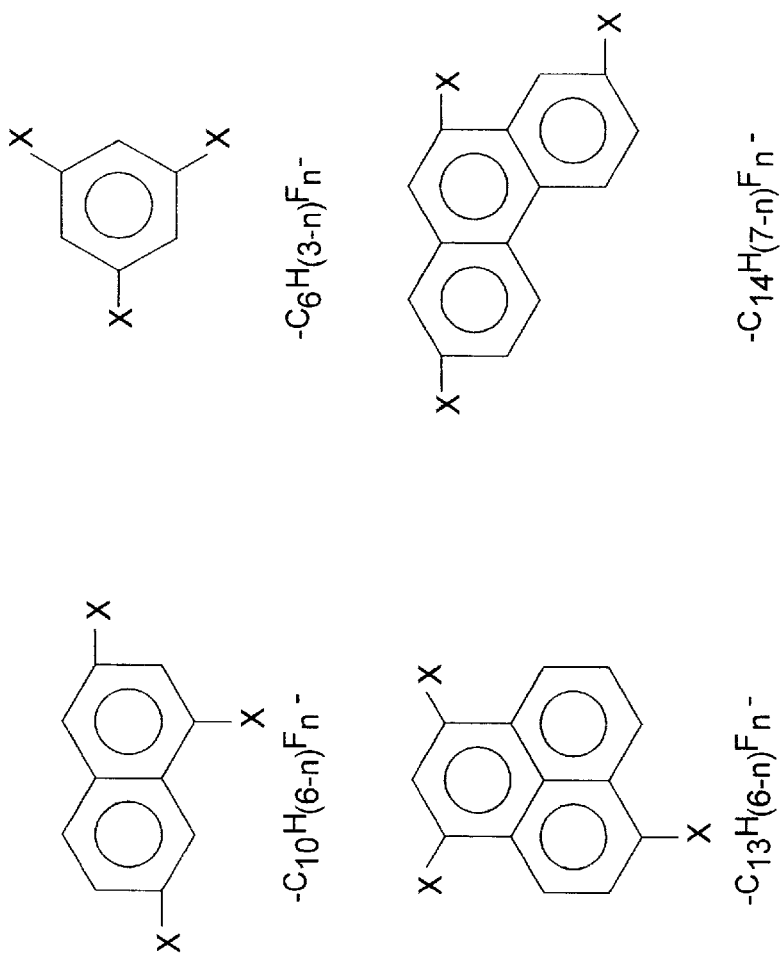
FIG. 6 depicts some tri-functional aromatic moieties of this invention.

To form cross-linked polymers of this invention, we describe three types of precursors. In addition to di-functional aromatic moieties, multi-functional moieties are useful for forming cross-linked polymer networks. Some examples of such tri-functional aromatic moieties are shown in FIG. 6. These aromatic moieties have the general structural formulas: (—$C_{10}H_{(5-n)}F_n$—), (—$C_6H_{(3-n)}F_n$—), (—$C_{13}H_{H(6-n)}F_n$—), and (—$C_{14}H_{(7-n)}F_n$—). The "X" groups are $CF_2Y$, wherein Y is —H, —Br, or $SO_2R$, where R is —H, alkyl, or aromatic groups. There are numerous positional isomers of each of these structural formulas, and each is considered to be part of this invention. Furthermore, multi-functional aromatic moieties with more than three functional groups are also considered part of this invention. These molecules, when cross-linked, tend to form large polymer sheets. The aromatic moieties are constrained by the covalent bonds linking them to other moieties of other polymer chains. Thus, these films will form strong polymer sheets. By depositing additional layers of polymer on top of each other, the π electrons of the aromatic moieties can interact with π electrons of adjacent polymer sheets, thus forming a very strong polymer matrix.

In another embodiment of this invention, multi-functional precursors are selected with the following chemical structures:

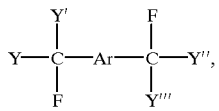

wherein Ar is a fluorinated aromatic moiety of at least 6 carbon atoms. wherein Y, Y', Y", and Y'" are leaving groups selected from the group consisting of —SR, —H, —NR$_3$, —SO$_2$R, —Cl, —Br, and —I, and wherein R groups are H, alkyl, or aromatic groups.

By selecting precursors with different Y, Y', Y", and Y'", and processing them to form reactive intermediates, multi-radical intermediates can be made. Cracking of these different C—Y, C—Y', C—Y", and C—Y'" bonds can be accomplished using combinations of excimer radiation or plasma, using apparatus such as shown in FIGS. 16 and 18–21. By selecting the wavelength of excimer radiation used, formation of radical intermediates can be tailored to the specific need. If additional C—Y bonds are to be broken, an additional energy source such as plasma can be used.

Upon deposition and polymerization of multi-functional radicals, cross-linked polymers are made. These cross-linked polymers have higher thermal stability, are stronger, and therefore have mechanical properties making them well suited for making integrated circuits of small feature size. Because they are made of fluorinated moieties, their dielectric constant is also low.

The degree of cross-linking can be varied by selecting desired leaving groups. The degree of cross-linking is also varied by selecting the appropriate ratios of precursors which form bi-functional radicals and precursors which form multi-functional radicals upon cracking. Increasing the proportion of multi-functional precursor increases the degree of cross-linking.

Moreover, the degree of cross-linking can be varied by varying the degree to which the precursors are cracked. An incompletely cracked multi-functional precursor will have fewer cross-linking bonds available than a fully cracked multi-functional precursor. Thus, the physical and electrical properties of polymer films can be adjusted to suit the particular need of the user.

An alternative way of manufacturing cross-linked polymers is to manufacture a thin layer of polymer on a wafer using bi-functional precursors and then exposing the wafer to radiation of an appropriate wavelength to photolyze selected C—Y bonds within the polymer. This permits cross-linkinig of polymers through bonding of adjacent reactive groups.

It is also possible to cross-link polymers after their deposition on wafer surfaces. These reactions are carried out by exposing the polymer to UV light for several seconds up to several minutes. [Sharangpani and Singh, *DUMIC*: 117–120 (1997), incorporated herein fully by reference.]

Other types of multi-functional compounds are also useful. To obtain amorphous thin films or thin films with a large proportion of amorphous phase, multi-functional compounds (Compound V) are used as precursors:

In the above, the Ar is an aromatic radical consisting of at least 6 carbon atoms. The Y groups arc selected from —SO$_2$R, —H, —Cl, —Br and —I, preferably, —H and —Br. The R is an alkyl group such as —CH$_3$ and n is an integer of at least 2 but no more than the allowable carbon numbers for sp$^2$C—X substitution in the Ar groups. Here, X is —H, —F or —CF$_2$Y in Compound V. which is prepared using Reaction 2 using a multi-functional aldehyde starting material.

When this Compound V is dissociated into reactive intermediates, the Y groups leave, resulting in the creation of a multi-functional intermediate molecule, which can polymerize into linear chains which cross-link with adjacent chains, thereby forming a 3-dimensional lattice network, herein termed a "super-lattice structure." For these multi-functional compounds, the aromatic moieties are not involved in the bonding. Thus, the aromatic moieties are free to rotate about their bonds, and this rotational freedom enables them to form more tightly packed configurations than molecules in which the aromatic moieties are more constrained. This precursor permits the addition of spacer moieties (CF$_2$) between the aromatic groups of adjacent polymer chains.

A. Super-Lattice Structures

When the multi-functional Compound V is used in transport polymerization, the resulting polymers will form three dimensional (3D) networks which can be characterized as Super-Lattice Networks (SLN). Examples of various lattice structures that can be found in SLIN are illustrated in FIGS. 8–13. [Stupp et al., *Science* 276:384 (Apr. 18, 1997), herein incorporated fully by reference.]

Figure 8:
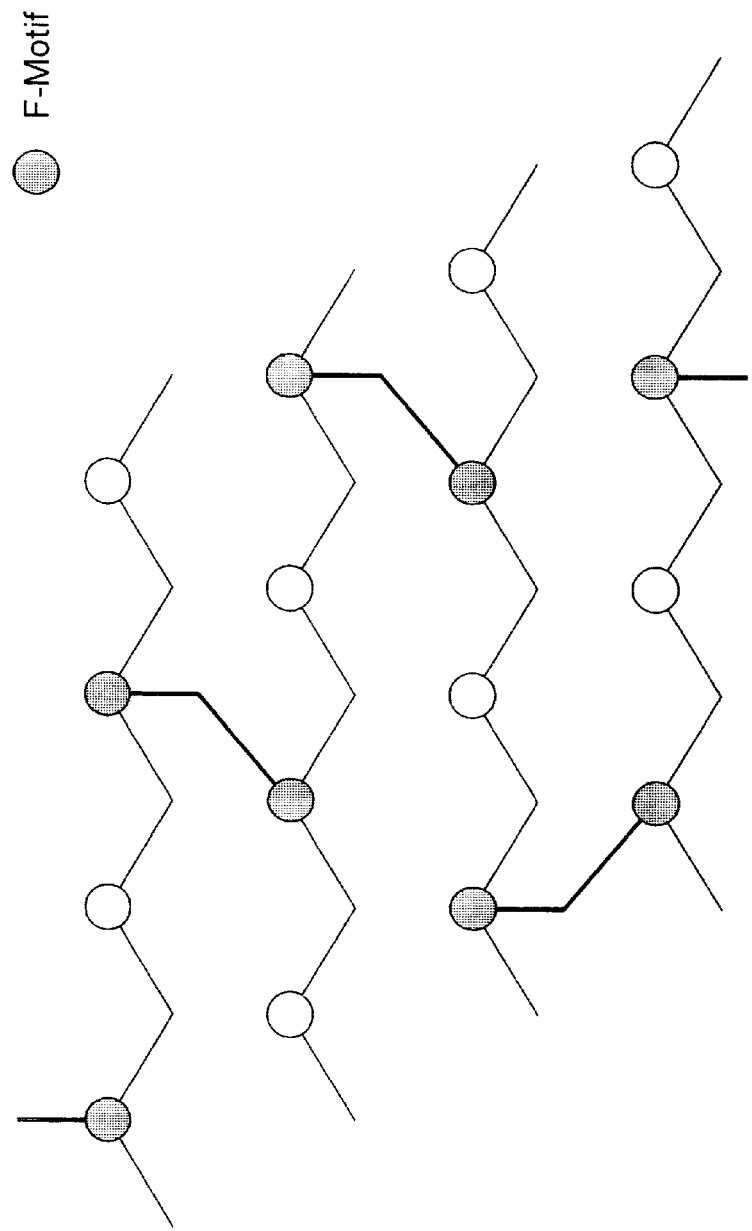
FIG. 8 depicts a 2×3 3-dimensional lattice network containing fluorinated moieties.

FIG. 8 shows a 3-dimensional network with a 2×3 lattice structure, wherein the "F-motif" is a fluorinated aromatic moiety.

Figure 9:
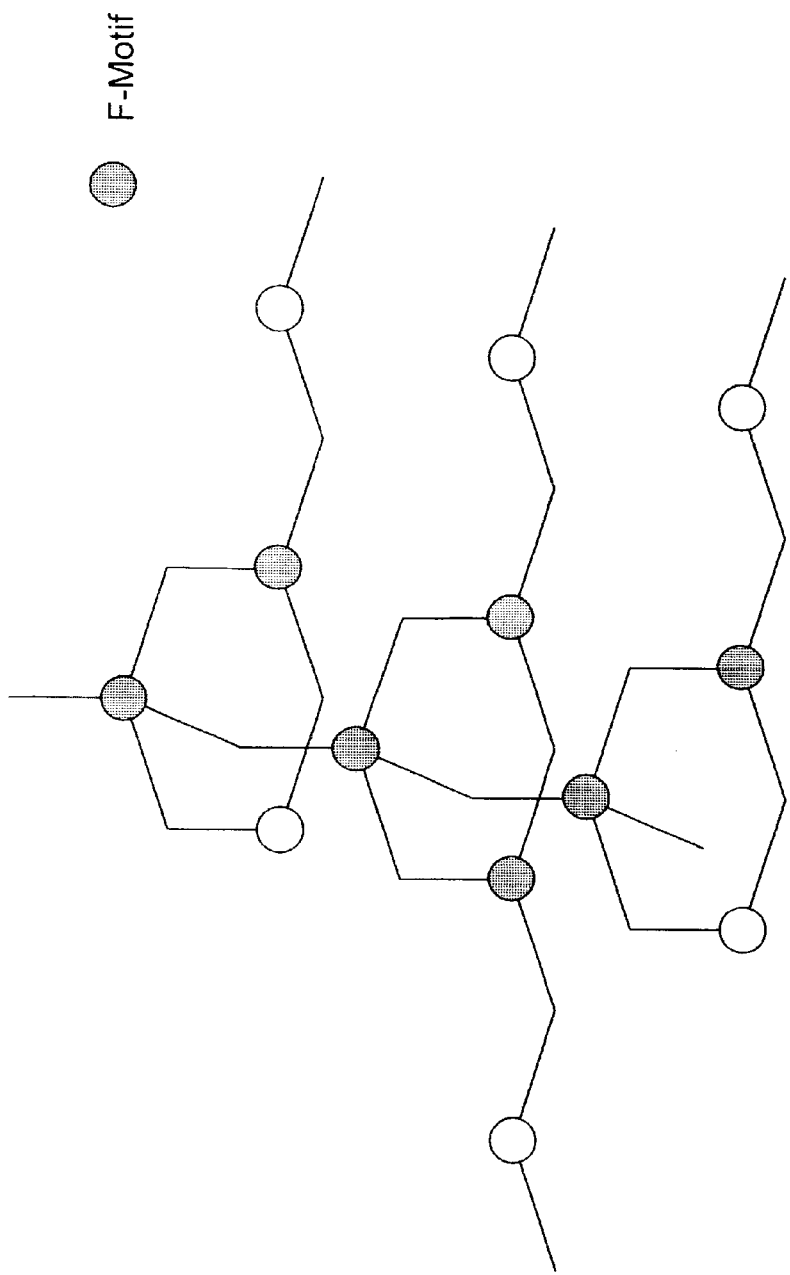
FIG. 9 depicts 2×3×4 superlattice networks of this invention comprising fluorine containing aromatic moieties.

FIG. 9 shows a 2×3×4 super-lattice structure made from precursors of this invention, wherein the "F-motif" is a fluorinated aromatic moiety.

Figure 10:
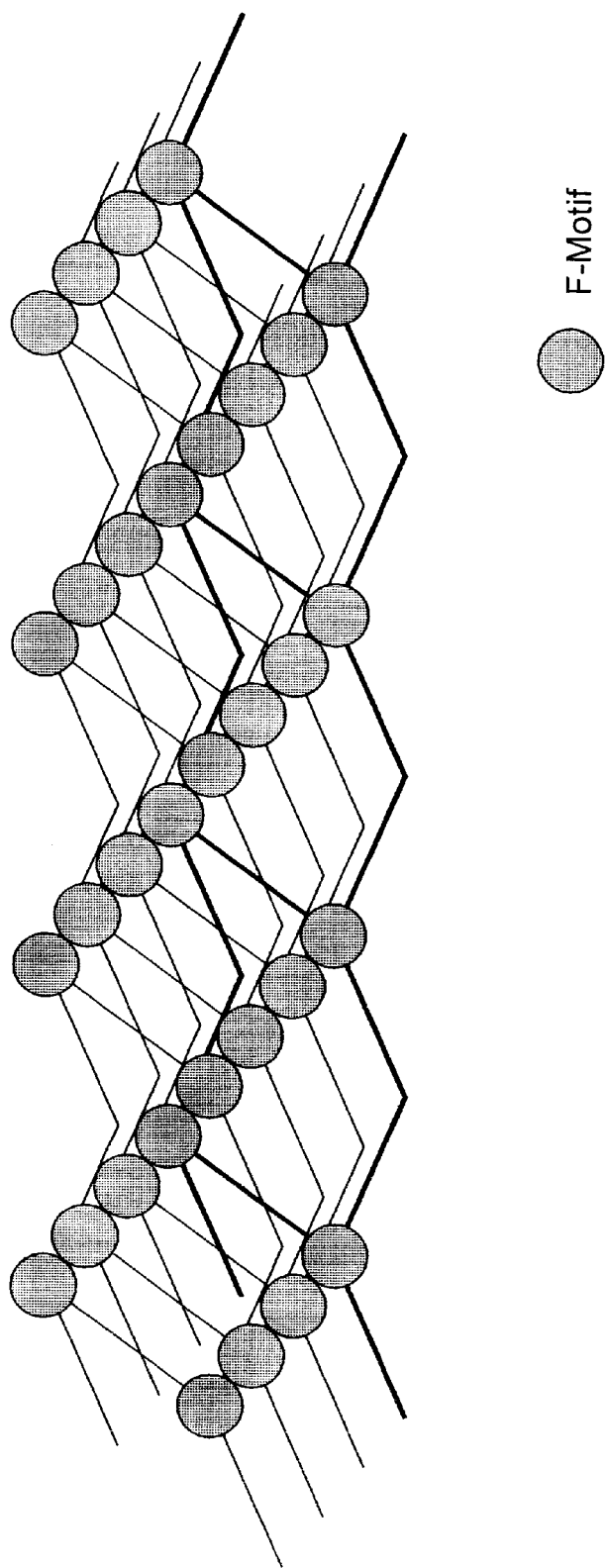
FIG. 10 depicts a 3×3 perfluoro super lattice network of this invention containing fluorinated aromatic moieties.

FIG. 10 shows a 3×4 super-lattice structure made from precursors of this invention, wherein the "F-motif" is a fluorinated aromatic moiety.

Figure 11:
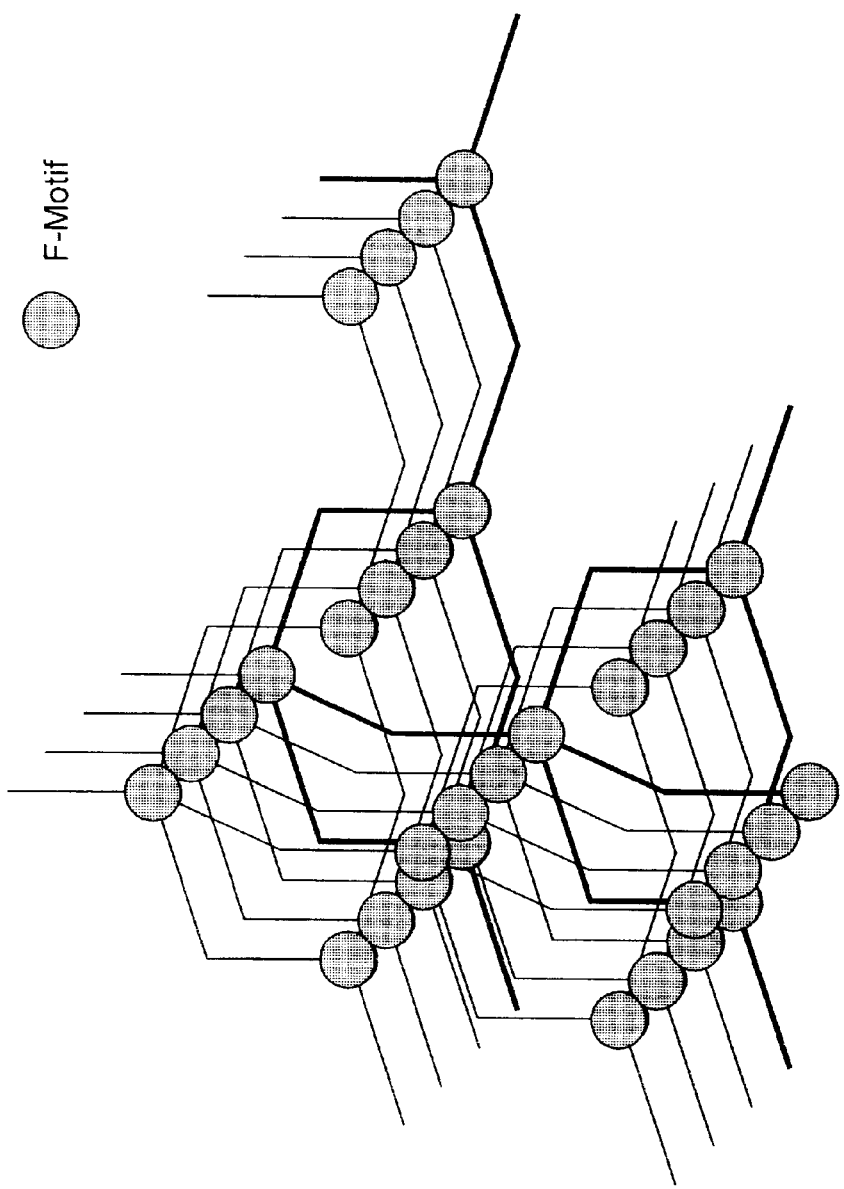
FIG. 11 depicts a 3×4 perfluoro super lattice network of this invention containing fluorinated aromatic moieties.

FIG. 11 shows a 3×4 perfluorinated super-lattice structure made from perfluorinated precursors of this invention, wherein the "F-motif" is a fluorinated aromatic moiety.

Figure 12A:
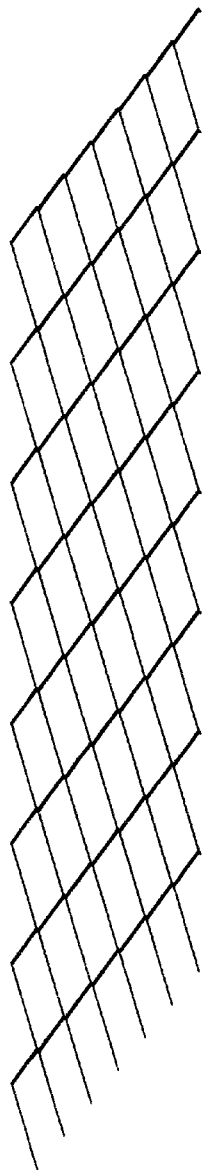
FIG. 12a depicts a lattice structure of polytetrafluoroethylene (top).

FIG. 12*a* shows the 3 dimensional structure of polymers of polytetrafluoroethylene (Teflon™) (top).

Figure 12B:
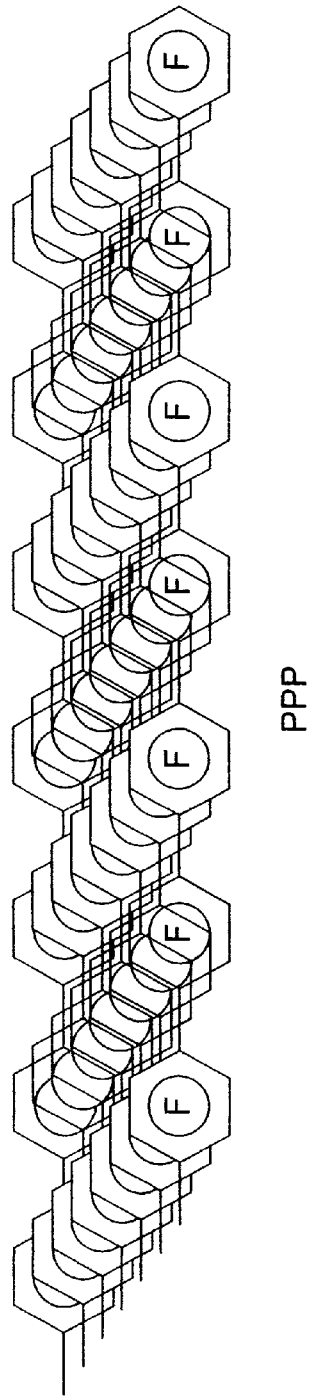
FIG. 12b depicts a lattice structure of made from poly (paraphenylene) (PPP); bottom).

FIG. 12*b* shows the 3 dimensional structure of polymers of poly(paraphenylene) (PPP).

The aromatic moieties (F-motifs) pack tightly together forming a stable array in which the π electrons of adjacent aromatic rings can interact, thereby stabilizing the structure. This increased stability increases Tg, Td, and increases the mechanical stability making semiconductor processing more controllable.

Figure 13:
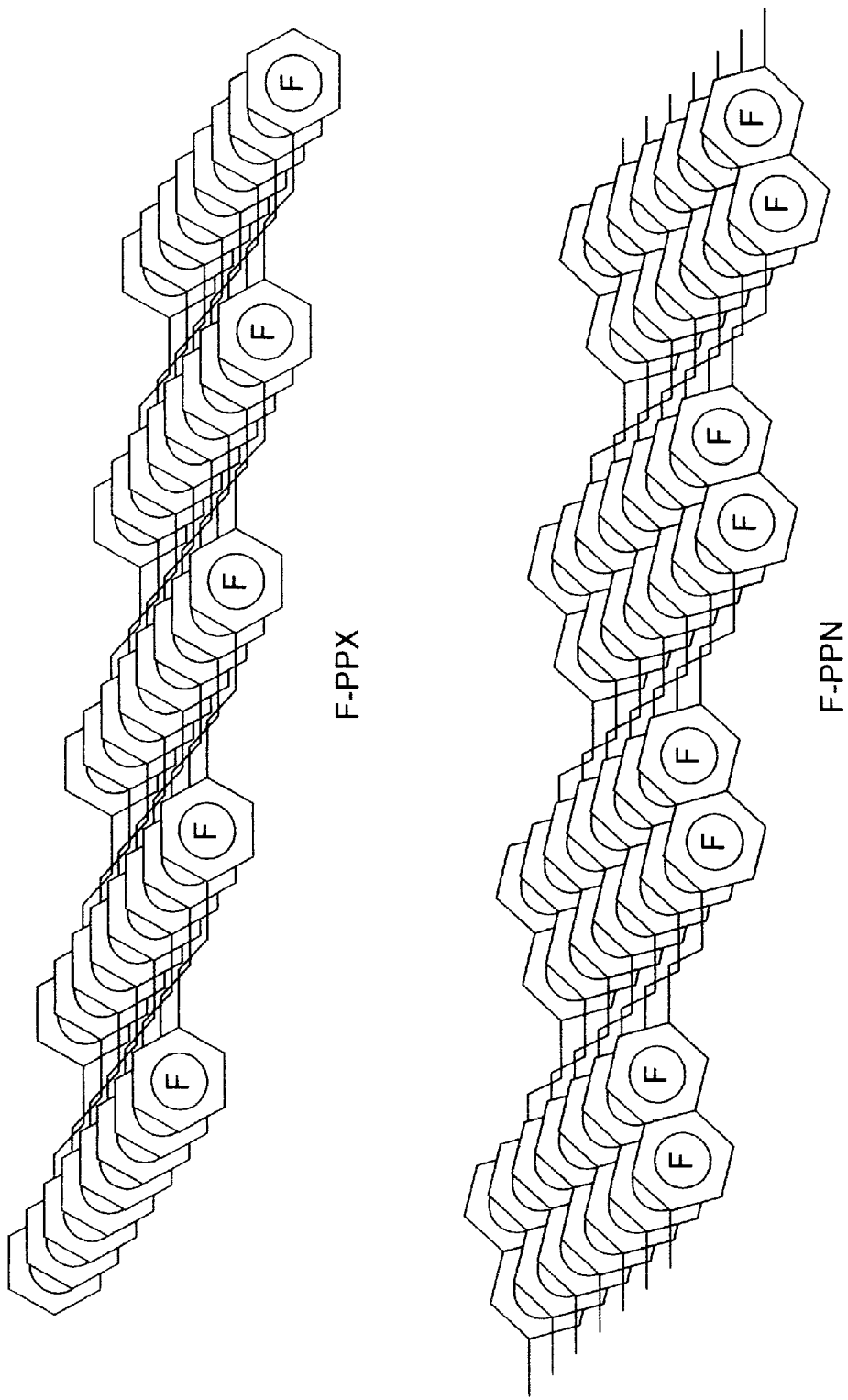
FIG. 13 depicts a comparison of lattice structures made from fluorinated poly(para-xylylene) (top) and fluoro-poly (para-naphthalene (F-PPN; bottom).

FIG. 13 shows a comparison between the super-lattice structures of fluorinated poly(para-xylylene) F-PPX and fluorinated poly(para-naphthylene) (F-PPN). The density of fluorine atoms in the F-PPN lattice, as well as the increased density of sp$^2$C—sp$^2$C, and sp$^2$C—F bonds increases Tg, Td, and improves the mechanical stability needed for semiconductor processing.

The dimensions of each lattice structure in the SLN can be relatively small (50–100 Å) comparing to that of a typical crystalline phase (several hundreds to thousands of Å). The overall SLN polymers show characteristics of amorphous material and no crystalline order can be observed from wide angle X-ray diffraction measurements.

Due to their locally ordered lattice structures, the SLN can result in high packing density and/or cohesive energy density than conventional amorphous or cross-linked polymers. The SLN can thus exhibit many desirable thermal stability and mechanical properties of crystalline polymers. When a multi-functional Compound V that has a higher symmetrical configuration is used, the resulting polymers would consist of a larger proportion of these SLN, therefore will potentially exhibit higher thermal stability and are stronger.

V. Methods of Manufacture of Polymers from Precursors

The reaction used for the cracking of the precursors of the invention are described in Reaction 6:

Reaction 6

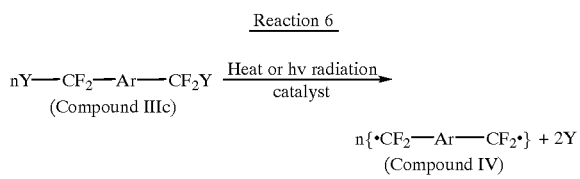

In general, Compound IIIc can be prepared from its corresponding dialdehyde using $SF_4$ or DAST as fluorinating agents (see Reaction 2).

The above tetrafluoro precursor Compound IIIc is fed into a transport polymerization system (FIGS. 14–21) where the precursor is dissociated (cracked) using an energy source such as heat, plasma or photons, and is then transported into a deposition chamber and is finally deposited onto the surface of a wafer where the idealized di-radical intermediates (Compound IV) polymerize into a thin film of fluorinated poly(para-fluoroxylylene) material with a low dielectric constant.

The above precursor can also be used in a chemical vapor deposition (CVD) system. There, the precursor is placed directly on the wafer, which is then exposed to heat or light energy which cracks the precursor into intermediates (Compound IV), which then polymenrize into a thin film.

These precursors (Compound IIIc) offer several advantages over the prior art. First, the monomeric compound (IIIc) where Y=H is cheaper and more readily available than the dimer, $(—CF_2—Ar—CF_2—)_2$ or the di-bromo compound (IIIb). Next, the inclusion of fluorine atoms in the aromatic moiety confers greater thermal stability and mechanical strength and decreases the dielectric constant of the resulting polymer. Moreover, precursors which can form cross-linked polymers confer greater strength to the polymer One theory for the increased thermal stability of the fluorinated compounds of this invention is that the bonding energies of the $sp^2C═sp^2C$, $sp^2C—F$ and $sp^2C-sp^3C$ bonds of 145, 126, and 102 keal/mol. respectively, are higher than that of $sp^3C—H$ bonds (88 keal/mol). A possible additional theory is that the $sp^3C—F$ bonds may also be involved in hyperconjugation with $sp^2C═sp^2C$ double bonds of the adjacent phenylene groups in the fluorinated poly(para-xylylene). This hyperconjugation renders a higher bond energy for the $sp^3C—F$ bonds than that found in non-hyperconjugated $sp^3C—F$ bonds.

Furthermore, brominated precursors generate molecular bromine, an environmentally unfriendly product. Replacement of Br by H results in the production of molecular hydrogen, which is environmentally friendly or can be burned easily and safely.

This invention can also offer higher yields because the side product, molecular hydrogen, has a lower atomic weight than bromine.

Transport Polymerization and Chemical Vapor Deposition of Fluorinated Aromatic-Containing Polymers Transport Polymerization (TP) and Chemical Vapor Deposition (CVD) of materials generally involves a multi-step process, wherein a precursor is cracked to form a reactive intermediate, and the reactive intermediates then can polymerize.

Transport polymerization begins with the cleavage of precursors to form reactive intermediates in one chamber. The reactive intermediates are then transported into a different chamber or to a different location in the same chamber for deposition on a substrate (usually silicon or silicon dioxide with metal features). In contrast, CVD processes occur in a single chamber wherein the dissociation of precursor and polymerization of polymer occur directly on the wafer. CVD is generally described in P. Van Zant, *Microchip Fabrication, A Practical Guide To Semiconductor Processing*, $3^d$ edition, McGraw Hill. San Francisco (1997), incorporated herein fully by reference.

There are several types of TP and CVD which are defined by the energy sources used to crack the precursors. Thermal TP or CVD use heat energy, usually derived from a resistive heater. Infrared TP and CVD use IR radiation to heat the precursors. Photon assisted TP and CVD utilize the principal that light energy of certain wavelengths can break interatomic bonds resulting in the formation of the reactive intermediate radicals. Plasma enhanced TP and CVD utilizes plasma energy, derived from an electrical field generated by radio frequency or microwave energy. High density plasma TP and CVD (HDPTP and HDPCVD) also use energy derived from radiofrequency generators. The types of TP and CVD processes useful for practicing the present invention are shown in Table 1.

TABLE 1

Methods Used for Depositing Precursors of Low Dielectric Polymers

| | Thermal | Photon Assisted | Plasma Enhanced |
|---|---|---|---|
| TP | ** | ** | * |
| CVD | Impossible | Possible | ** |

Table 1 shows the preferred (**) methods for depositing precursors of this invention. Thermal CVD is currently impossible because the high temperatures needed to crack the precursor damage the aluminum metal lines and polymers on the wafers. Photon assisted CVD is possible, as is plasma enhanced transport polymerization (*). The methods and equipment are described below and in co-pending application entitled "New Deposition Systems and Processes For Transport Polymerization."

A. Thermal Transport Polymerization

All current commercial poly(para-xylylenes) are prepared from thermolysis of its corresponding dimers (2,2 paracyclophanes) using the Gorham method. The dimers are cleaved in a furnace operated at temperatures ranging from $_{600}°$ C.to 800° C. to generate the needed reactive intermediates or di-radicals. Similarly, thermolytic or photolytic methods can be used to make polymers using the precursors of this invention. The thermolytic and photolytic processes generate reactive intermediates by breaking the C—Y bonds in the precursor, Compound IIIc. Because the C—F bonding energy is stronger than that of the C—Y bond, in principle, thermolysis for this reaction can be very effective at splitting the C—Y bonds, and can generate fluorinated di-radicals necessary for polymerization of the intermediates into fluorinated polymers. Thermal processing can be achieved using a transport polntnerization system (FIG. 14) which is prior art, or by using new transport polymerization systems (FIGS. 15–20), which are new and novel.

Figure 14:
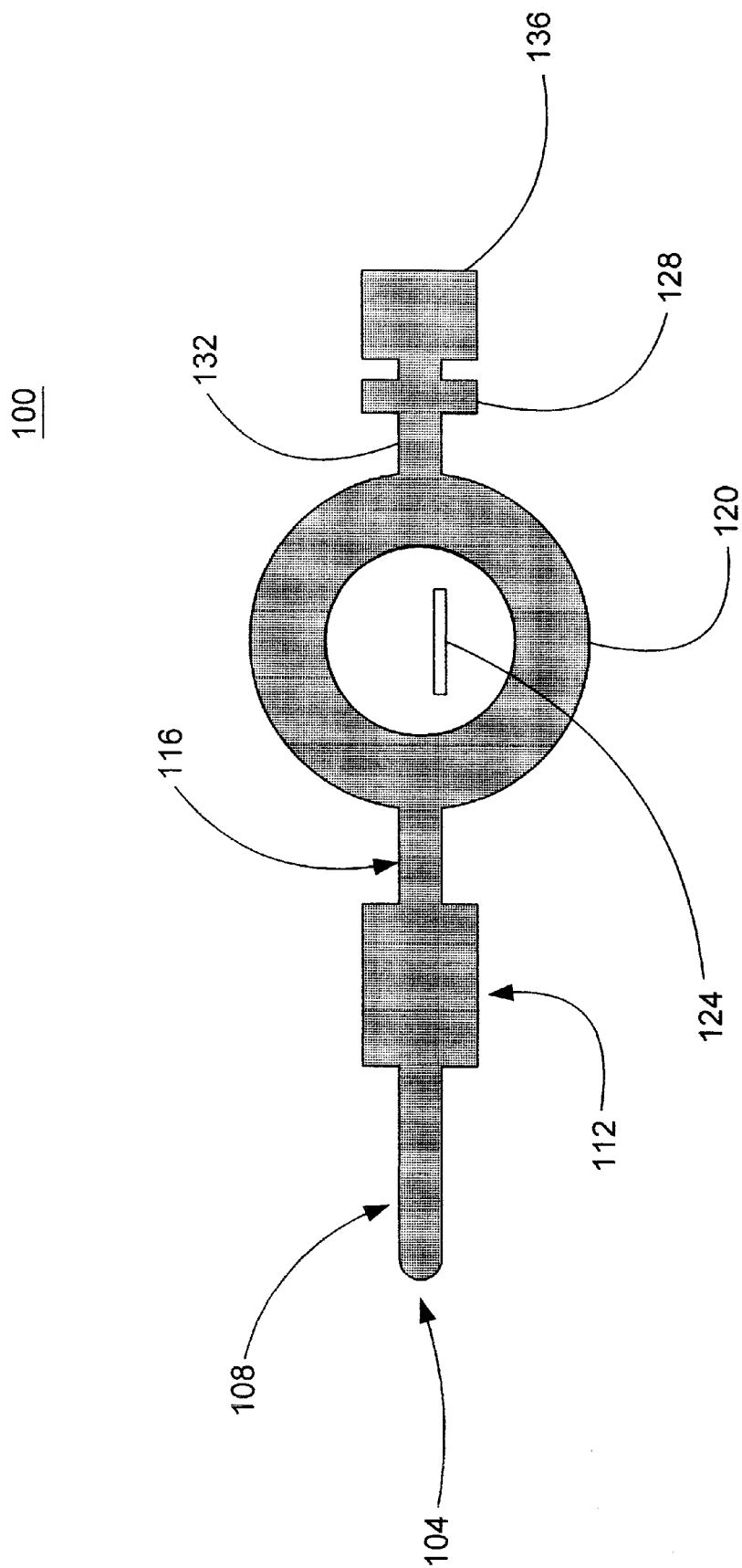
FIG. 14 depicts prior art equipment for transport polymerization of polymers.

FIG. 14 shows a general diagram of a prior art transport polymerization system 100 using solid dimers. A door 104 permits the placement of precursors into the vaporizer 108. The vaporized precursors are transported to the pyrolyzer 112, where the precursors are thermally cleaved into reactive intermediates. The intermediates are then transported via a pipe 116 to the chamber 120 and chuck 124, where the intermediates polymerize on the wafer surface. A valve 132 permits the chamber pressure to be lowered by a dry pump 136 keeps the pressure of the system low, and the cold trap and mechanical chiller 128 protects the pump from the unpolymerized molecules in the chamber.

Figure 15:
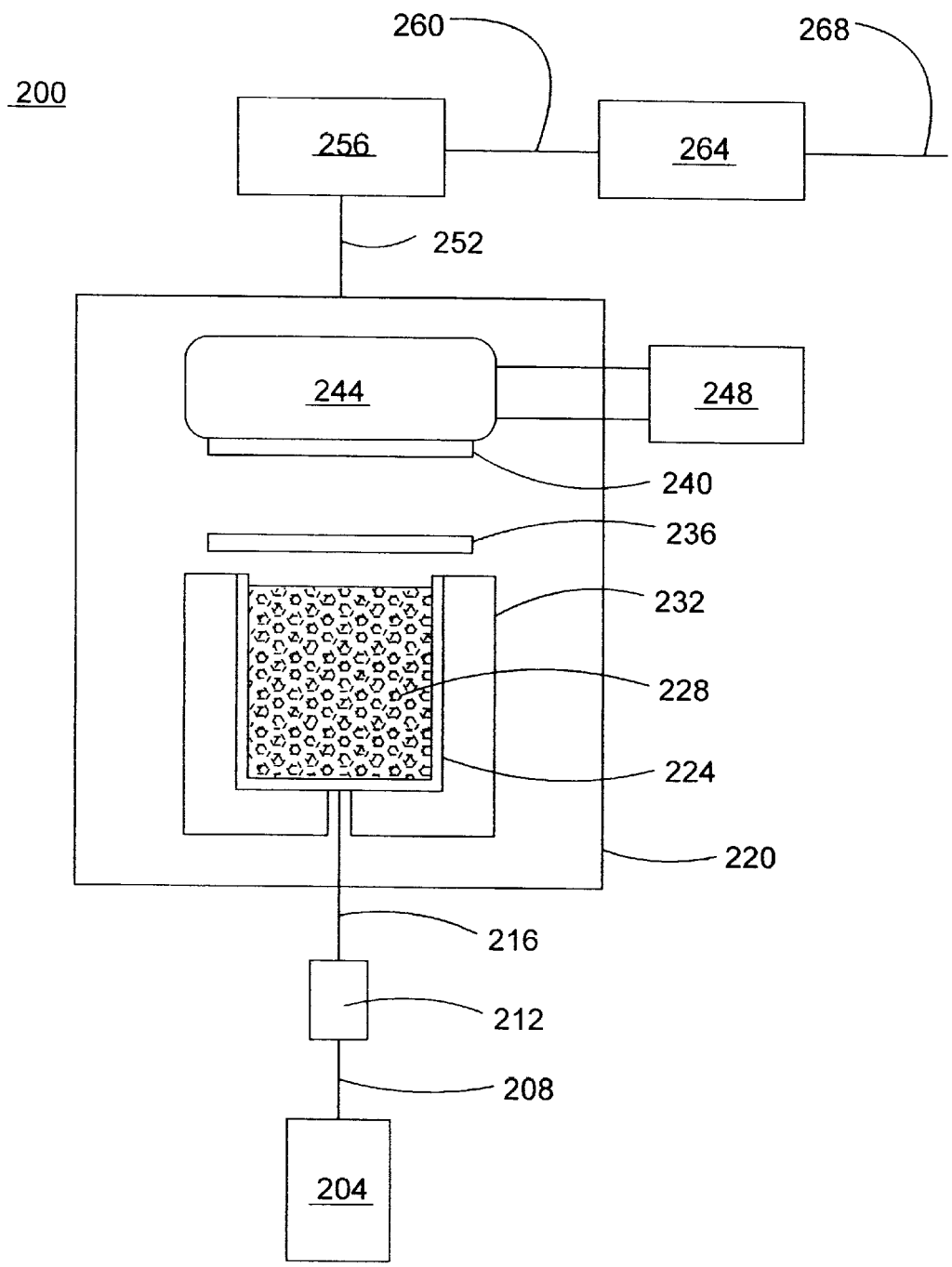
FIG. 15 depicts an embodiment of the invention having a single chamber used for thermolytic transport polymerization (TTP) of polymers.

FIG. 15 shows a more specific schematic diagram of a novel transport polymerization system 200 using a resistive heater. The liquid precursors are contained within a precursor tank 204, flow through a pipe 208 into a mass flow controller 212, are controllably released through another pipe 216 and into the chamber 220. The chamber includes a container (cracking device) 224 which can be adapted to hold a catalyst 228 which will be described below. The precursor molecules are transported into the cracking device and are heated by a resistive heater 232 to generate the reactive intermediates. After leaving the cracking device, the intermediates are dispersed by a diffusion plate 236 to disperse the intermediates evenly over the wafer surface 240.

The intermediates deposit upon the wafer 240, which is held on a cold chuck 244 which in turn, is connected to a chiller 248 to maintain the temperature of the chuck and wafer below the condensation temperature of the intermediates. The pressure in the chamber 220 is reduced by a pump 264 connected via a pipe 260 to a trap 256, which is connected to the chamber 220. The trap 256 prevents molecules from depositing inside the pump 264.

Pyrolysis of novel precursors of this invention results in reactive intermediates comprising mostly di-radicals. These intermediates are then transported to a deposition chamber (FIG. 14). The chamber wall is kept at temperatures ranging from 60° C. to 150° C. to prevent deposition on the chamber wall. Deposition of thin polymer films will be largely confined to the wafer as long as the wafer is maintained at relatively low temperatures. A mechanical or electrostatic cold chuck therefore is used to hold the wafer and maintain the desired wafer temperatures. The range of temperatures is from about −40° C. to about 30° C. The ceiling temperature that an intermediate will condense on the wafer surface depends upon its chemical structure and the degree of vacuum. For tetrafluorobenzene di-radicals, the ceiling temperature ranges from about 30° C. to about 50° C. when the chamber pressure is in the range of from about 20 milliTorr to 100 milliTorr. The wafer deposition temperature determines not only the deposition rate, but also the mechanical properties of the resulting polymer. For example, PPX-N deposited at lower temperatures (below −20° C. to −30° C.) have lower elastic modulus and higher elongation when reaching the break point, due to lower crystallinity compared to PPX-N deposited at higher temperatures.

Depending on the temperatures and pressure in the pyrolyzer, thin films consisting primarily of either linear or highly cross-linked fluorinated polymers can be obtained. For instance, under higher pyrolyzer temperatures (>750° C.), cross-linked F-PPX tends to result from cracking of C—F bonds of the Compound IIIc. To generate cross-linked polymers, wherein H is a leaving group, it is necessary to select conditions favoring elimination of H and some of the F atoms, thereby creating multi-radical intermediates. For precursors in which the leaving group Y is H, and when catalysts are not used, temperatures of about 700° C. to about 800° C. are desirable. When catalysts are used, temperatures can be as low as about 400° C. When Y is Br or $SiR_3$, the ideal temperatures are from 500° C. to 850° C. Upon deposition on the wafer, these multi-radical intermediates form cross-links with adjacent polymer chains, thereby increasing the mechanical strength and thermal stability of the resulting polymer film.

Alternatively, to generate more linear polymers, the use of —SR and —$NR_3$ as leaving groups is preferred because their bonds can be selectively broken at different temperatures. At low pyrolysis temperatures (<700° C.), the SR and $NR_3$ groups will be eliminated, resulting in intermediates which deposit and form mostly linear polymers. When Y is SR, or $SO_2R$, temperatures in the range of 450° C. to 700° C. are desirable. At higher temperatures (>750° C. to about 800° C.), F atoms can be eliminated also, forming multi-radical intermediates. As with those formed from H-containing precursors, the multi-radical intermediates can deposit to form polymers which are cross-linked.

The time needed to complete the pyrolysis ranges from a few milliseconds to several hundred milliseconds.

1. Catalysts

The temperatures and times needed to complete pyrolysis can be reduced by employing a catalyst in the chamber. There are three types of catalysts useful for this invention. They include dehydrogenation catalysts, debromination catalysts, and desulfurization catalysts. The type of catalyst used is dependent upon the leaving group of the precursor.

An ideal catalyst useful for this invention should provide high reactivity, high selectivity, long process life cycle, high recycle capability, and less severe pressure and temperature requirements. It should be inexpensive, safe for human handling, and should be environmentally friendly. The catalyst should crack or cleave the C—Y bond without cracking or cleaving the C—F bonds if linear polymers are desired. Further, the catalyst should not add any metal or metal compound into the dielectric film during deposition. Serious reliability problems occur when a metal contaminant resides within the dielectric materials.

a. Dehydrogenation Catalysts

When Y is —H, any commonly used dehydrogenation catalyst is suitable. These catalysts are also called "protolytic cracking catalysts", or "oxidative dehydrogenation catalysts", in petroleum processing. Additionally, most "dehydrocyclization catalysts" and some of the "aromatization catalysts" for hydrocarbon processing are also useful for this invention, because aromatization normally involves dehydrogenation.

Potassium ferrite ($KFeO_2$) on iron oxide is an example of a suitable catalyst which is commercially available. The ferrite commonly comprises a promoter that may contain a salt of oxide of a Group (IIA) metal, such as Mg, Ca, or Sr, and a Group VB or VIB metal, such as V, Nb, Cr, Mo. or W. [See J. I. Krochiwitz ed., *Encyclopedia of Chemical Technology*, 4th edition, Catalysis and Catalysts, Vol. 5: 320 (1991), incorporated herein fully by reference.] These catalysts can be useful at temperatures up to about 600° C. Variations of these catalysts are BASF's Lu-144F™ and Shell 105™ catalysts, and catalysts for the dehydrogenation of ethylbenzene. These include those produced by Monsanto-Combustion Engineering-Lumis, Union Carbide-Cosden-Badger, and Societe-Chimique des Charbonnages. [See J. J. McKetta, Ed., *Encyclopedia of Chemical Processing and Designs: Dehydrogenation,* Vol. 14:276, Marcel Dekker Inc. (1992), incorporated herein fully by reference.]

Other industrial catalysts include Cu and Zn oxides on alumina and Cu, Ag or Cu-Ag alloy in the form of gauge or as metal deposited on a low surface area support such as kaolin, clay and active carbon. Other supports or carriers can include asbestos, pumice, kiesselguhr, bauxite, CuO, $Cr_2O$, $MgCO_3$, $ZrO_2$, and zeolites. These catalysts are active by virtue of an oxide layer on the metals, and are used for hydrogen generation from methanol. Catalysts consist of copper chromite, bismuth molybdate, iron molybdate, or tin phosphate on similar supports are also useful. [See J. I. Krochiwitz ed., Encyclopedia of Chemical Technology 4th edition, Catalysis and Catalysts, Vol. 5: 320 (1991); J. J. McKetta, Ed., *Encyclopedia of Chemical Processing and Designs:* Dehydrogenation. Vol. 14:276, Marcel Dekker Inc. (1992). Both of these references are incorporated herein fully by reference.]

In addition to dehydrogenation catalysts, reforming catalysts used in petroleum reforming processes can also be used. A first group of these include transition metal oxides, such as $V_2O_5$, $MoO_3$, $WO_3$ and $Cr_2O_3$ in bulk form or preferred on a non-acid support such as silica, neutral alumina or active carbon. [See Meriaudeau and Naccache, *Cat. Rev.-Eng. Sci.* 39(1&2):5–48 (1997), incorporated herein fully by reference.] Typically useful catalysts include Shell 205™, which consists of 62.5% $Fe_2O_3$, 2.2% $Cr_2O_3$, and 35.3% $K_2CO_3$, and Dow Type B™ catalyst which consists of calcium and nickel phosphates promoted With a small amount of chromium oxide.

An additional group of catalysts useful for dehydrogenation include noble metals on acid supports. The most commonly used catalysts are Pt (0.3 to 0.7%) and Pt/Re on a chlorided (acidified) alumina (e.g., γ- or η-$Al_2O_3$). The bimetallic Pt/Re-alumina is preferred for its longer life time. In addition, Pt, Ga or Au modified H-ZSM-5™, or Pt on medium-pore Zeolite support such as In-ZSM5™ is also very effective.

Other, multimetallic reforming catalysts include Pt/Re catalysts of the above including lesser amounts of Ir, Ga, Ge, Sn or Pb supported by chioridated alumina. The catalysts typically have surface areas ranging from 170 $m^2$/g to 300 $m^2$/g and pore volumes ranging from 0.45 $cm^3$/g to 0.65 $cm^3$/g. [See J. I. Krochiwitz ed., *Encyclopedia of Chemical Technology,* 4th edition, Catalysis and Catalysts, Vol. 5: 320 (1991).] Additionally useful catalysts can also be found in the OJG International refining catalyst compilation-1987 [J .J. McKetta ed., Encyclopedia of Chemical Processing and Designs: Petroleum Processing, Catalyst Usage, Vol 35:87–89 Marcel Dekker (1992).] These catalysts comprise active agents such as Pt/ReCl, Ni, PtCl and other rare earth metals on alumina and zeolites. The above references are incorporated herein fully by reference.

In addition to the catalysts mentioned above, many variations are possible. Notably, these catalysts include noble metals or metal sulfide on active carbon, (2) $Ga_{13}$, $Cr_{12}$, $GaAl_{12}$ & $Al_{13}$ on PILCs, (3) M—$Al_2O_3$ with M=lanthanides, (4) $Al_2O_3$ kneaded with M, where M is Bi & Sb compounded with periodic table Group VIB & VIIB metals, (5) M-modified H-ZSM-5 and H-ZSM-11 where M is Zn, Ga, Pt-Ga, Pt-Na, Mo, Cr, K, Ca, Mg, Al, and Group VIII metals, (6) M-modified MFI (H-GalloSilicates) where M is Si/Ga, Na/Ga, Al, (7) rare earth metal exchanged Y-zeolites or Ultra stable Y-zeolites. (8) Ti oxide paired with Zr oxide, (9) M plated onto aluminum, where M is Ni, and Ni, Cr, and Al alloys.

Pure dehydrogenations are endothermic by 15 to 35 kcal/g-mol and hence have high heat requirements. The above catalysts are normally used at temperatures ranging from 300° C. to 600° C. depending on the residence time of the chemicals in the reactor. The effective temperature for some of these catalysts can be lowered by adding free radical initiators such as I, $Br$,. $H_2O$, sulfur compounds or oxygen and their mixtures. However, special care should be taken to avoid reaction of desirable di-radicals faith free radicals generated from these initiators. This can be achieved by providing large mean free paths for these reactants in the reactor, reducing residence time and the adjustment of wafer temperatures to avoid condensation of low mass free radicals.

b. Debromination and Desulfurization Catalysts

When Y is Br or $SO_2R$, catalysts can be found in Hertler et al., *J Org. Chem.* 28: 2877 (1963), U.S. Pat. No. : 3,268,599 (1966), Show et al., *J. Appl. Polym. Sci.* 13:2325 (1969). Chow et al., J. Org. Chem. 35(1):20 (1970). These references are incorporated herein fully by reference. When H is Br, and copper is a catalyst, the pyrolytic temperatures can be decreased from 550° C. to 350° C. Other catalysts include Rh, Pt, and Pd.

c. Loss of Catalyst Function

With time, catalysts may lose reactivity due to changing their oxidative state or coke formation. The life time of the catalysts can be increased at high operating temperatures or high partial pressure of hydrogen. If catalysts lose activity by coke accumulation, they can be regenerated by careful oxidation followed by reduction with hydrogen before being returned to service. [See: J. J. McKetta ed., *Encyclopedia of Chemical Processing and Designs:* Catalysis and Catalysts Vol. 6:420; *Petroleum Processing, Catalyst Usage,* Vol 35:89 Marcel Dekker, Inc. (1992), incorporated herein fully by reference.]

B. Transport Polymerization Using Electromagnetic Radiation

In addition to thermal methods for dissociating precursors, electromagnetic radiation is useful for practicing this invention. Useful electromagnetic radiation is in the infrared (IR), ultraviolet (UV) and vacuum ultraviolet (VUV) spectra. UV and VUV produce no heat, whereas IR produces heat. When used in combination, IR and either UV or VUV can dissociate precursors with increased efficiency.

Figure 16:
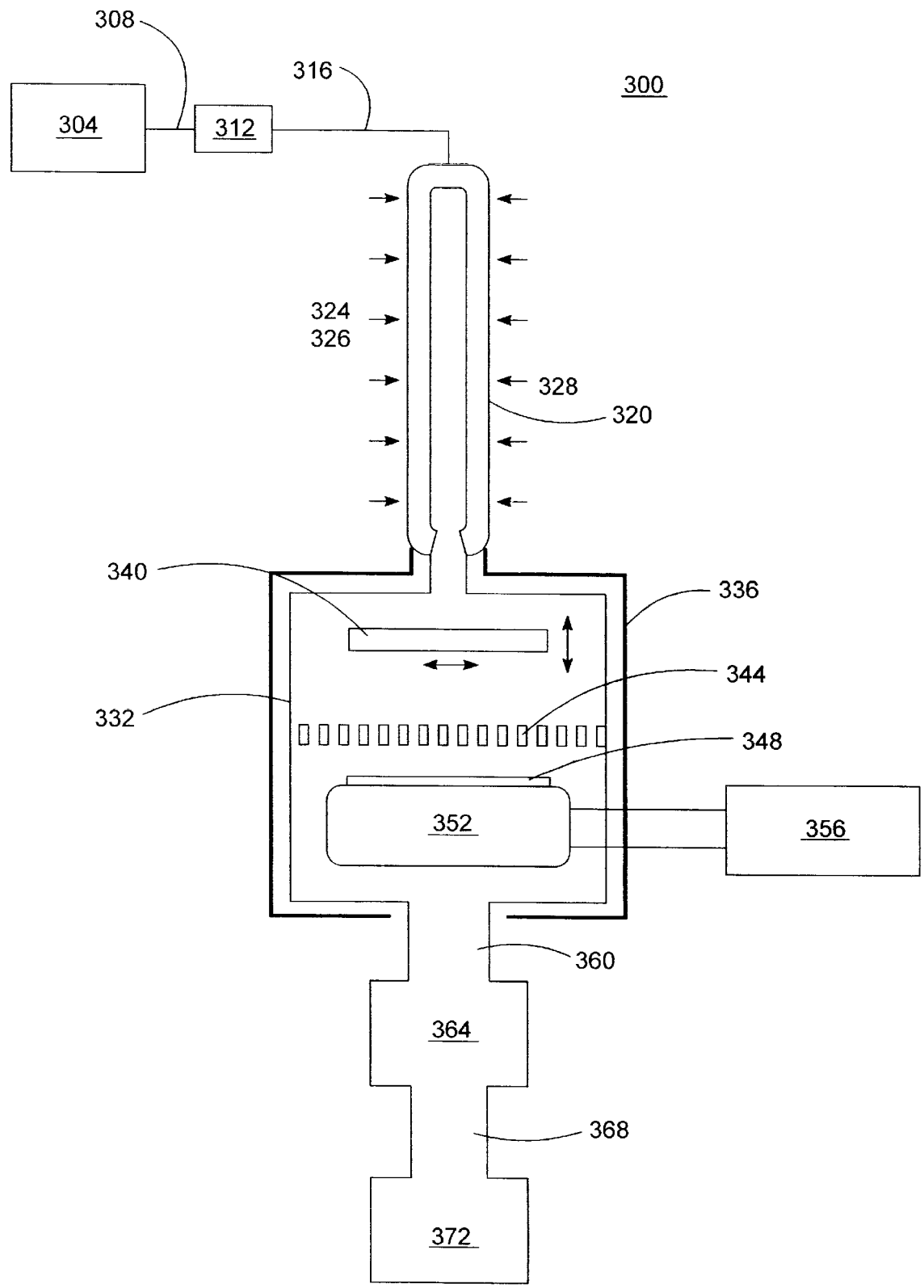
FIG. 16 depicts an embodiment of the invention used for photon assisted transport polymerization (PATP) of polymers using ultraviolet (UV), vacuum ultraviolet (VUV), and/or infrared (IR) radiation sources.

FIG. 16 is a schematic diagram of a transport polymerization system 300 using elcctromagnietic radiation as an energy source for cracking precursor molecules. Precursors are transported from the precursor tank 304 through a pipe 308 and through a mass flow controller 312 through another pipe 316 and into a tube 320 which is transparent to the types of electromagnetic radiation to be used. For IR irradiation, a glass tube is sufficient. For UV irradiation, quartz tubes are necessary, and preferably are made of a single crystal quartz. For VUV irradiation, tubes made of $MgF_2$, LiF, or $CaF_2$ are necessary because the short wavelengths of VUV cannot pass easily through quartz.

After dissociating in tube 320, the reactive intermediates are transported into the deposition chamber 322 surrounded by a heater 336. The wall of the chamber is heated to decrease the deposition of molecules on the chamber wall. This heating can be accomplished by any conventional means, including, but not limited to resistive heating. After entering chamber 332, the flow of intermediates is adjusted by a movable flow pattern adjustor 340. Vertical movement of the flow pattern adjustor 340 adjusts the flow rate of intermediates into the chamber 332 and aids in mixing the intermediates more evenly within the chamber 332. Horizontal movement of flow pattern adjustor 340 adjusts the flow distribution of intermediates over the wafer 348. The flow pattern adjuster can be a flat, stainless steel plate, or alternatively can be a porous or honeycomb structure. A gas dispersion plate 344 evenly disperses the flow of intermediates over the wafer 348. Dispersion holes between the flow pattern adjuster and the wafer ensure the dispersion of the intermediates. The wafer 348 is held by a cold chuck 352. which is cooled by any chiller 356 employing any conventional means, including, but not limited to liquid nitrogen or reverse Peltier effect. A UV or VUV source also can be directed toward the wafer 348 to permit cross-linking of polymers after their deposition. A pipe 360 is for exhausting the chamber 352. and a pump 372 connected via a pipe 368 to a trap 364 maintain the pressure within the chamber at desired levels.

1. Photon Assisted Transport Polymerization of Fluorinated Poly(Para-Xylylenes)

In this invention. photolyic methods of geierating radical intermediates are preferred (FIG. 16). Using the photolytic method, the above Reaction 6 can be very selective and efficient if appropriate photon sources are used. The photon sources can be provided by ultraviolet (UV) light generated by mercury vapor discharge or metal halide lamps.

Exemplary sources of UV radiation for transport polymerization can include (1) a mercury lamp that provides from 50 to 220 mW/cm$^2$ of UV ranging from 185 to 450 nm or (2) a metal halide lamp that provides from 40 to 160 mW/cm$^2$ of UV ranging from 256 nm to 450 nm. These UV sources provide photon energies ranging from 2 to 5 eV, which are sufficient for generating radical intermediates.

An alternative to conventional UV light is vacuum ultraviolet (VUV). [See Kogelschatz and Eliasson, "Microdischarge Properties in Dielectric-Barrier Discharges," Proc. Symp. High-Pressure Low-Temperature Plasma Chemistry (Hakone. Japan) Aug.: 1–8 (1987), hereby incorporated fully by reference.] Incoherent excimer radiation can provide a large number of tN and VUV wavelengths for photolytic processing of various chemicals. The preferred source is incoherent excimer radiation derived from dielectric barrier discharge. UV and VUV photons that are in the ranges of 3 to 5 eV are especially useful. These energy levels are comparable with the bonding energies of most chemical bonds, thus are very effective for initiating photochemical reactions (see Table 2).

TABLE 2

Bond Energies of Selected Bonds

| Chemical Bonds | Bonding Energies (eV) |
|---|---|
| $\phi\text{-CH}_2\text{Br}$ | 2.52 |
| $\phi\text{-CH}_2\text{—OR}$ | 3.52 |
| $\phi\text{-CH}_2\text{—CH}_3$ | 3.30 |
| $\phi\text{-CH}_2\text{—NH}$ | 3.09 |
| $\phi\text{-CH}_2\text{—F}$ | 4.17 |
| $\phi\text{-CH}_2\text{—SR}$ | 3.20 |
| $\phi\text{-CH}_2\text{—H}$ | 3.83 |

Table 2 shows the bonding energies in electron volts (eV) corresponding to certain bonds of this invention. This data is from Streitwiesser et al., Introduction to Organic Chemistry, Appendix II, University of California Press, Berkeley, Calif. ( 992). incorporated herein fully by reference.

However, the energies of mercury vapor or metal halide UV radiation are too small to be useful for rapid transport polymerization. The desired residence time within the cracking chamber which is the time available for photolysis should be in the range of a fews milliseconds to several hundred milliseconds. Therefore, VUV is the most desirable form of energy for photon assisted transport polymerization.

VUV or incoherent excimer UV sources can be provided by dielectric barrier or silent discharge using a variety of gas or gas mixtures according to methods known in the art. For example, VUV can be generated using KrBr, $Ar_2$, ArCl, ArBr, $Xe_2$ and $F_2$ gases. Xe emits at 172 nm, Kr at 222 nm, and XeCl emits at 308 nm. As can be seen from Table 2, nearly all of the chemical bonds of interest in polymer manufacture can be broken using photolytic methods. Because excimer radiation is selective for the energy of the specific bonds, excimer radiation from a second source or alternatively, a plasma source may be used simultaneously if it is desired to break other bonds at the same time. Such a combination of excimer sources and plasma sources are useful to break bonds of precursors for making cross-linked poly(para-xylylenes). Because the leaving groups of these precursors can be different, it is desirable to break those bonds selectively to generate tri- and tetra-functionai reactive intermediates.

Using photon-assisted processes of this invention, it is also possible to cross-link the novel polymers after their deposition. By directing the photons toward the surface of polymer, the electromagnetic energy disrupts some of the C—F or C—H bonds, creating radicals, which can bond with nearby polymer chains, resulting in a cross-linked film of polymers. This can be accomplished by exposing the wafer to UV or VUV for several seconds up to several minutes.

2. Transport Polymerization Using Infrared (IR) Radiation

Figure 3:
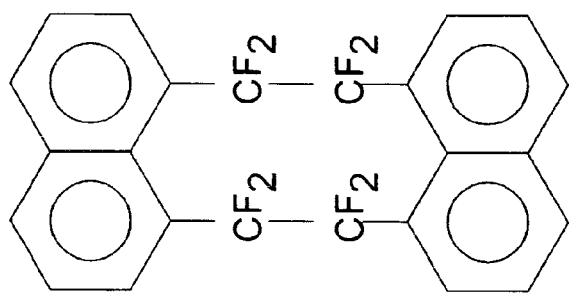
FIG. 3 depicts some of the side products obtained by reaction of (1,3) isomer of naphthalenyl moieties.
Figure 3:
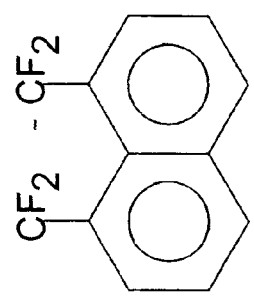
Figure 3:
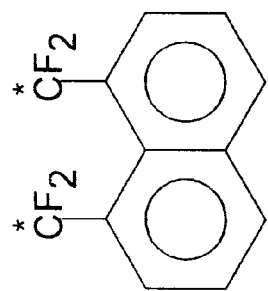
Figure 17:
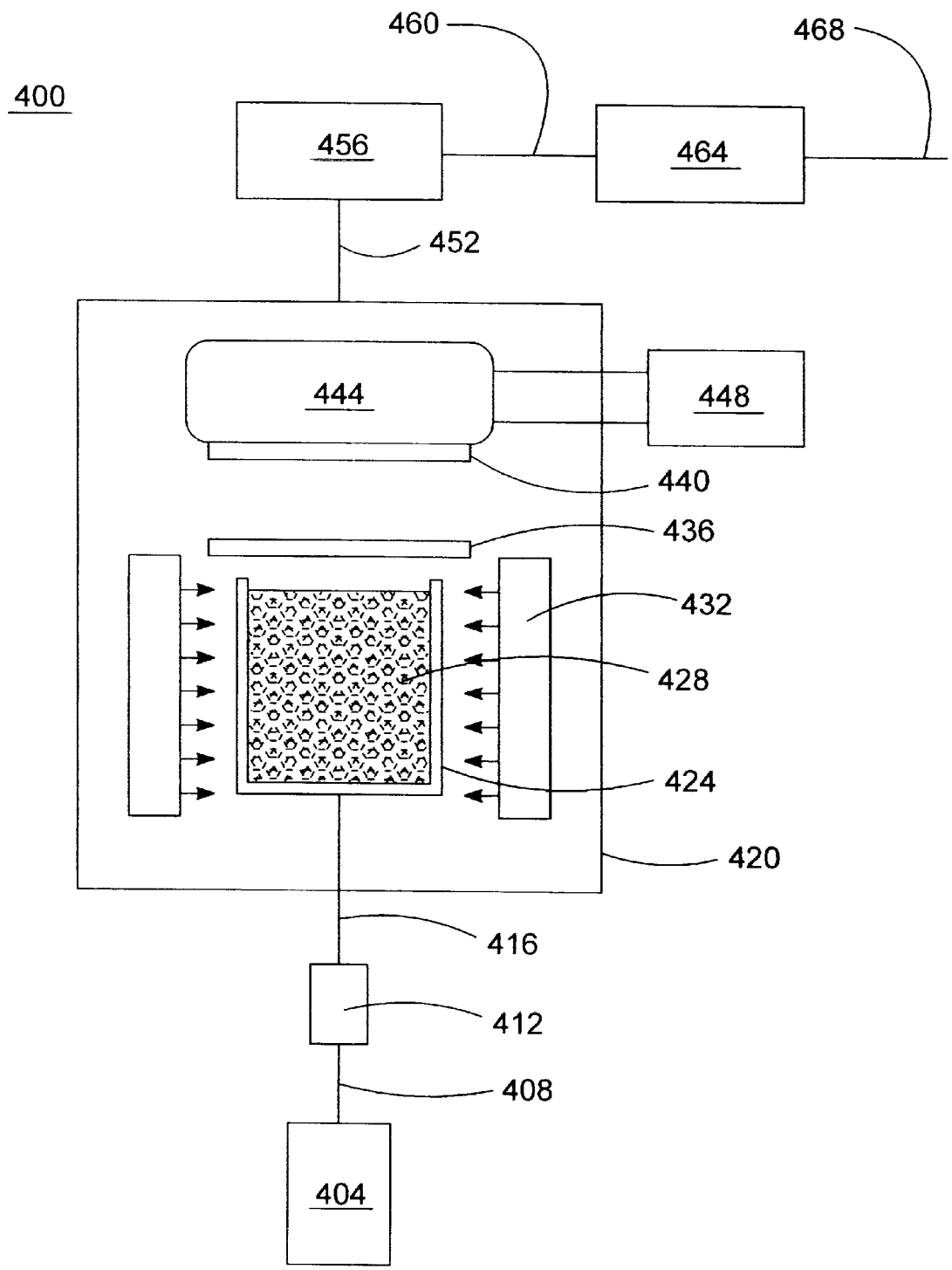
FIG. 17 depicts an embodiment of the invention used for transport polymerization using infrared (IR) radiation.

An alternative transport polenirization system employing IR radiation 400 is shown in FIG. 17. The precursors are transported from a precursor holder 404 through a pipe 408 and through a mass flow controller 412 and a second pipe 416 into the chamber 420. The chamber contains a quartz chamber 424, optionally containing a catalyst 428. An infrared radiation source 432 is placed outside the quartz container 424, and the precursors are dissociated as they pass through the quartz container 424. A diffusion plate 436 is used to optimize the flow pattern of intermediates to the wafer 440. Optionally, a flow pattern adjuster as shown in FIG. 3 (340) may be used to adjust the flow of intermediates over the wafer 440. The wafer 440 is held on a cold chuck 444, which is cooled by a conventional chiller 448. The pressure in the chamber is maintained by a pump 464 connected via a pipe 460 to and a trap 456, which is connected to chamber 420 by a pipe 452. The trap 456 protects the pump from deposition of intermediates in the pump 464.

IR radiation is preferred over resistive heating because of higher heating rate, lower cost, more uniform heating [See P. Singer, Semiconductor International March 1996: p 64; A. Dip, Solid State Technology, June 1996, page 113), incorporated herein fully by reference.] In IR radiation, a combination of both thermolytic and photolytic reactions are expected. The IR power should be in the range of from 150 to 500 Watts, preferably from 300 to 400 Watts, and most preferably 350 Watts.

3. Plasma Enhanced Transport Polymerization

Plasma energy is also used to dissociate precursors into reactive intermediates. There are generally two types of energy sources for plasma enhanced transport polymerization or chemical vapor deposition. They are radiofrequency (RF) and microwave sources.

Figure 18:
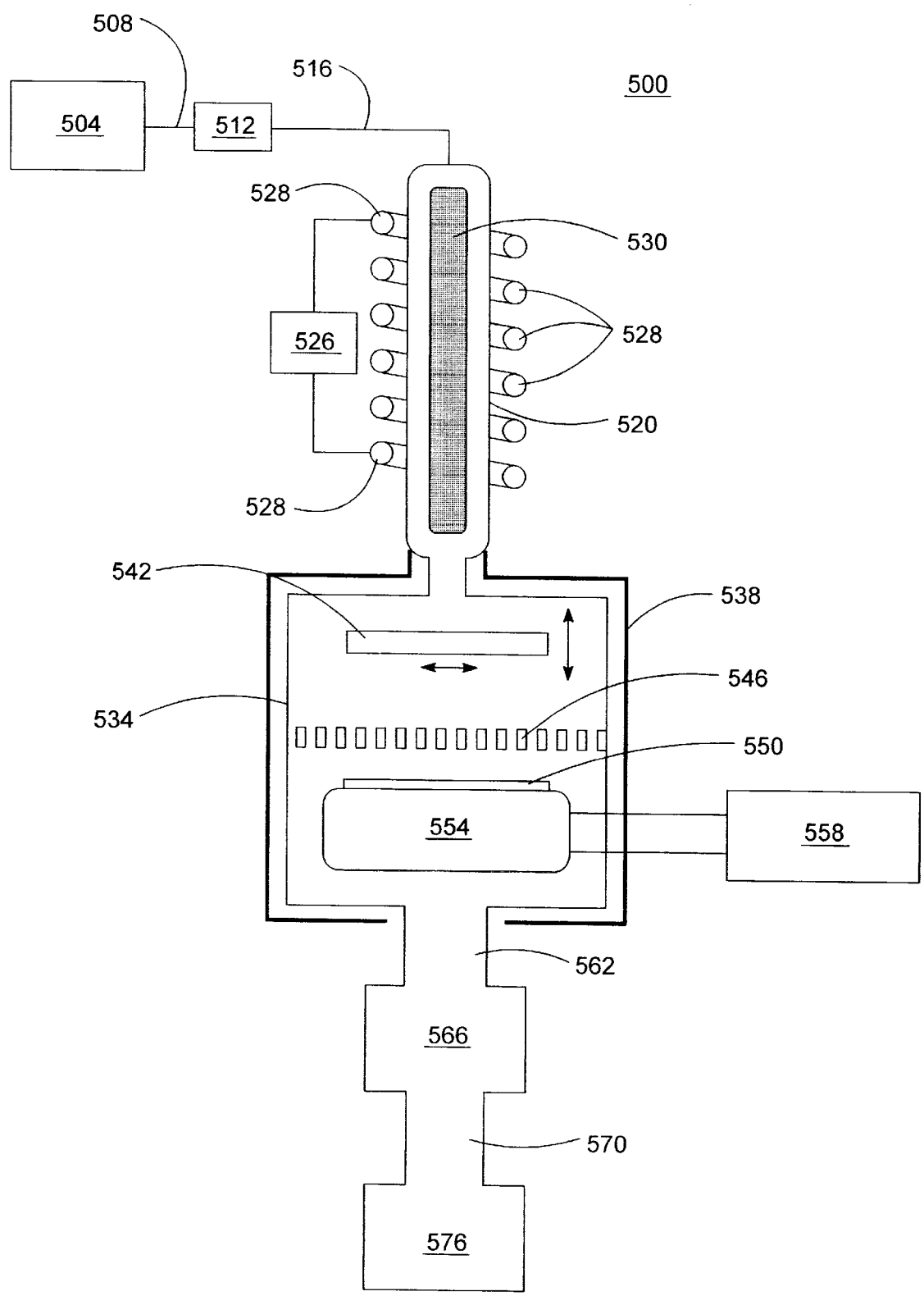
FIG. 18 depicts an embodiment of the invention used for radio frequency (RF) plasma enhanced transport polymerization (PETP) of polymers.
Figure 19:
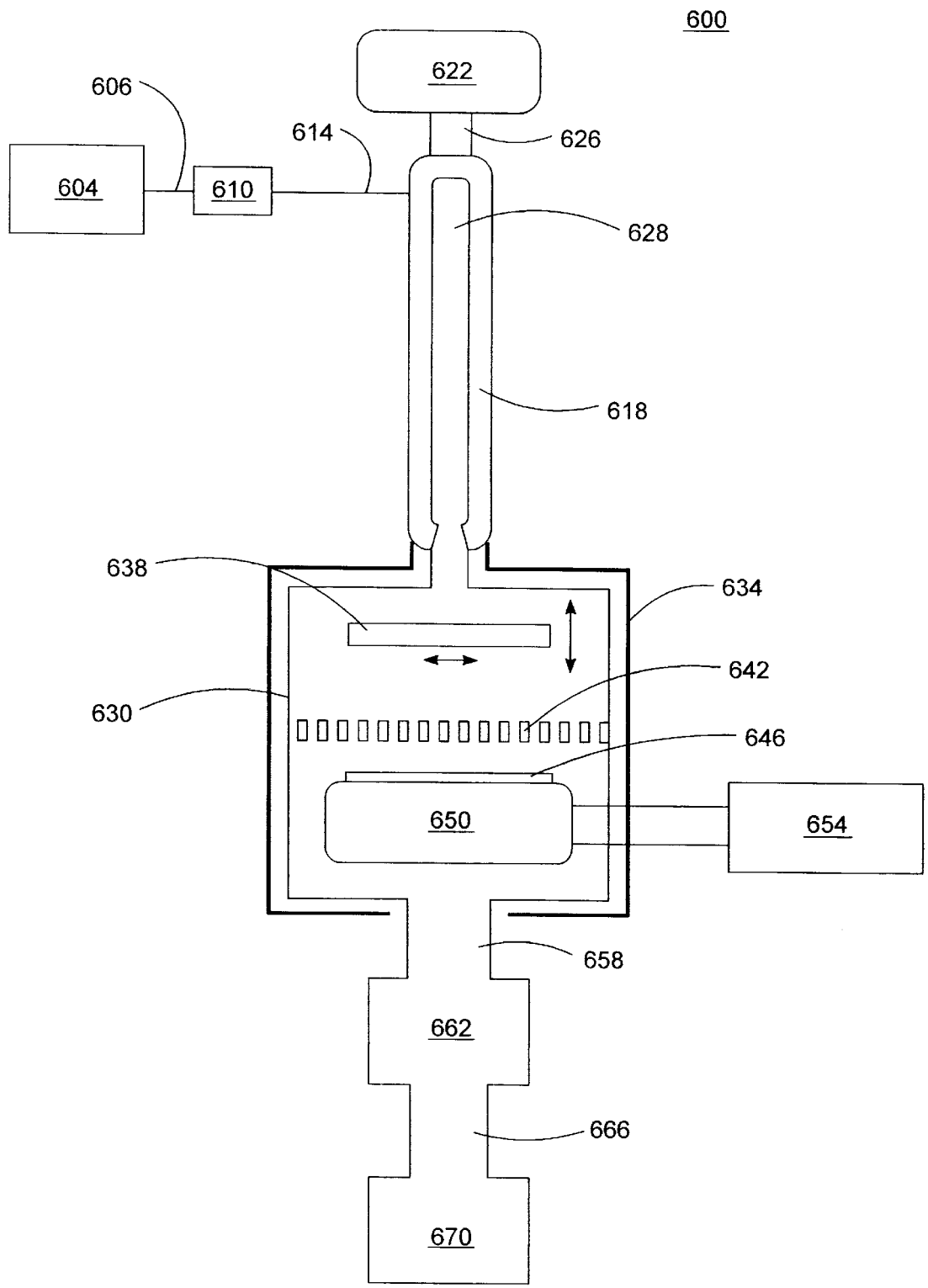
FIG. 19 depicts an embodiment of the invention for microwave plasma enhanced transport polymerization (PETP) of polymers.
Figure 20:
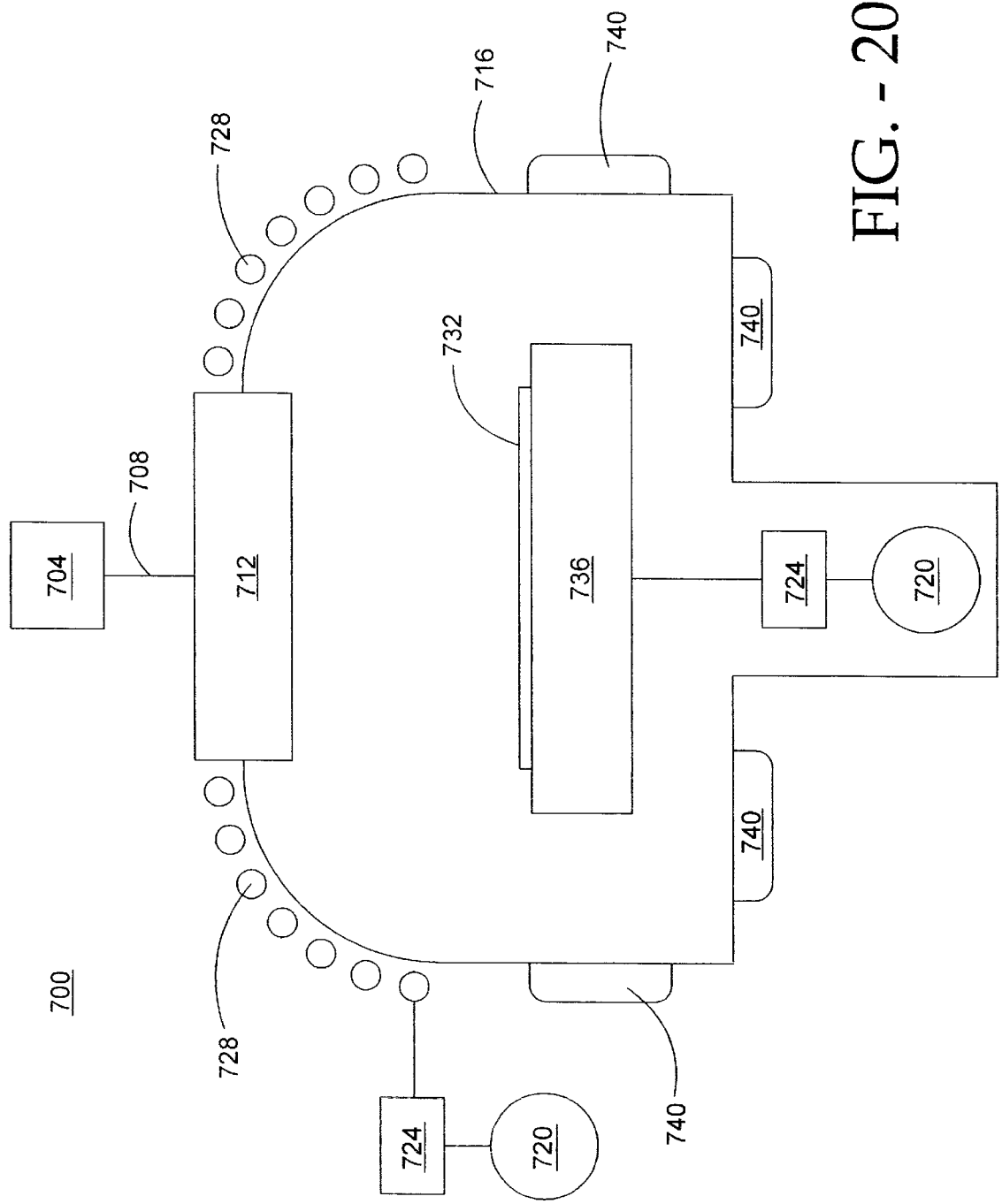
FIG. 20 depicts an embodiment of the invention for high density plasma enhanced transport polymerization of polymers.

Plasma enhanced TP is carried out using the novel reactors described herein (FIGS. 18–20). With low density plasma, the electron density in the plasma is in the range of about $10^{12}$ to about $10^{13}$ electrons/cm$^3$. Low density plasma TP and CVD can be carried out at about 100 milliTorr to about 100 Torr. High density plasma (HDP) is characterized by electron densities in the range of about $10^{13}$ to about $10^{14}$ electrons/cm$^3$. High density plasma TP and CVD can be carried out at pressures of about 0.1 milliTorr to about 100 milliTorr. The higher electron density in HDP increases the formation of cross-linked polymers, because the higher energy density increases the numbers of tri-radical intermediates which can form cross-links between polymer chains.

a. Plasma Enhanced Transport Polymerization Using a Radio Frequency Plasma Generator FIG. 18 is a schematic diagram of a transport polymerization system 500 employing RF to generate a plasma. The precursors are stored in a precursor holder 504, are transported via a pipe 508 and through a liquid injector for liquid precursors, or a mass flow controller 512 for gases, then are transported via another pipe 516 into a plasma tube 520 made of quartz. Preferably, the tube 516 is made of a single quartz crystal. Precursors are exposed to RF energy generated by a RF generator 526, through a coil 528, and a plasma 530 is thereby generated. The plasma 530 then flows into a deposition chamber 534 which is surrounded by a heater 538. The heater 538 keeps the walls of the chamber 534 above the condensation temperature of the reactive intermediates. This prevents condensation of intermediates onto the walls of the chamber 534. The flow of intermediates is adjusted by a flow pattern adjuster 542. Vertical movement of the flow pattern adjuster 542 adjusts the flow rate of intermediates into the chamber 534, and aids in mixing the intermediates in the chamber 534. Horizontal movement of the flow pattern adjuster 542 adjusts the distribution of the intermediates over the surface of wafer 550. A gas dispersion plate 546 with holes distributes the flow of intermediates evenly over the surface of the wafer 550.

The wafer 550 is held on a cold chuck 554, which is kept cool by a chiller 558 employing any conventional cooling method, including liquid nitrogen and reverse Peltier effect. The chamber is connected via a pipe 562 to a cold trap 566, which traps undeposited intermediates. The pressure in the chamber 534 is maintained by a pump 576 connected to trap 556 by a pipe 570.

Frequencies needed to generate plasmas are in a range of from 1 kHz to 2.5 GHz. A preferred range is between 400 kHz and 13.56 MHz, with the most preferred frequency being 13.56 MHz. The power should be in the range of about 30 Watts to about 300 Watts. The preferred power range is about 100 Watts to about 250 Watts, and the most preferred power is about 200 Watts of discharge power. The pressure should be kept within a range of from 0.001 Torr to 100 Torr, preferably from 50 milliTorr to 500 milliTorr, and most preferably at 100 milliTorr. Alternatively, using low frequencies (5 kHz) can result in formation of insoluble poly(paraxylylene) which have a higher temperature resistance. [Morita et al. Trans. IEEE Japan pp: 65075 (1972), herein incorporated fully by reference.] A carrier gas such as nitrogen or argon is used, and the flow rates of the carrier gas should be from about 30 SCCM to about 90 SCCM preferably from 50 SCCM to 75 SCCM.

b. Plasma Enhanced Transport Polymerization Using a Microwave Generator

Microwave sources can also be used to generate plasmas for generating the reactive intermediates. FIG. 19 is a schematic diagram of a transport polymerization system employing microwaves. Precursors are held in a precursor tank 604, and are vaporized, pass through a pipe 606 and through a mass flow controller 610, through a second pipe 614 and into a quartz tube 618. A microwave generator 622 is attached via a waveguide 626 to one end of the quartz tube 618. Microwave energy enters the quartz tube 618 where a plasma 628 is generated, which dissociates the precursors into reactive intermediates. After dissociation, the intermediates are transported into a chamber 630 heated by a heating device 634, including, but not limited to resistive heater. The flow of the intermediates is controlled by, a flow pattern adjustor 638. Vertical movement of the a flow pattern adjustor 638 adjusts the flow rate of intermediates into chamber 630 and adjusts the mixing of intermediates in chamber 630. A gas dispersion plate 642 evenly distributes the intermediates over the surface of wafer 646. The intermediates deposit on the wafer 646, which is held by a cold chuck 650, which is attached to a chiller 654 employing any conventional cooling means, including, but not limited to liquid nitrogen or reverse Peltier effect. The chamber pressure is controlled by a pump 670, connected via a pipe 666 to a cold trap 662. The trap 662 is connected via a pipe 658 to the chamber 630. The cold trap 662 protects the pump 670 from deposition of intermediates.

Microwave power density or electron field strength is selected based upon the residence time of the precursors in the chamber. The power is generally between 200 and 700 Watts, preferably between 400 and 600 Watts. and most preferably at 500 Watts. Desirable electron energy is chosen to match the bond energy of the leaving group.

An inert gas such as argon can also be used in the new TP systems of the present invention. With inert gases in the chamber, the amount of oxygen can be reduced without going to very high vacuum. The reduction of oxygen content is important for reducing the formation of —C—O—C—, —C—O—O— and C—O—H bonds in the resulting polymer networks. Formation of these chemical bonds is known to increase dielectric constant, possibly due to higher polarity in C—O bonds comparing to that of C—C bonds. In addition. the more flexible C—O—C bonds will decrease the glass transition temperatures of the resulting polymers [See Chung J. Lee, "Polyimides, Polyquinolines and Polyquinoxalines: Tg-Structure Relationships", Rev. Macromol. Chem. Phys., C29(4):431–560 (1989)), incorporated herein fully by reference.] The presence of C—O—O or C—O—H bonds will also lower the thermal stability of the resulting polymers due to their ability to form C., .O—O. and .OH free radicals that will attack polymer chains and lead to polymer degradation.

In one option of this invention, the pressurized reactor can be avoided. In this case, the Compound IIIc can be prepared in a solution using DAST as described by Hasek et al., J. Amer. Chem. Soc. 82:543 (1960), incorporated herein fully by reference.

The Compound IIIc can be used therefore directly for current TP systems. In another option of the current invention, when a conventional furnace is used to split the Compound IIIa, a catalyst can also be placed in the furnace. Yet in another embodiment of this invention, when IR and VUV is used, a free radical initiator such as $Br_2$ or $I_2$ can be injected into the system to increase the yield or the efficiency of the above Reaction 1.

To prevent condensation of precursor, intermediates, or products on the chamber walls, the pressure within the reaction vessel should be below atmospheric pressure. Pressures in the range of 0.001 to 200 Torr work well. Furthermore to inhibit condensation of chemicals, the walls of the reaction chamber should be kept warm, preferably in the range of 50° C. to 150° C., preferably above 100° C. Although resistive heaters can be used, IR is preferably used along with VUV. The IR radiation heats the precursors to a threshold temperature, requiring less VUV power to complete the cracking reaction. IR also heats the chamber walls to decrease deposition on them because VUV is a cold light source which does not heat up the chamber.

Deposition and polymerization of reactive intermediates to form low dielectric polymers is achieved by placing the wafer on a cold chuck. The temperature of the cold chuck should be between −30° C. and 30° C., preferably at −5° C. Any suitable method for cooling the cold chuck may be used, including reverse Peltier, liquid nitrogen, or conventional refrigeration methods. Reverse Peltier and liquid nitrogen cooling methods are preferred. To prevent condensation of chemicals on the pump, a cold trap is placed between the vacuum pump and the deposition chamber.

c. High Density Plasma Chemical Vapor Deposition

Figure 21:
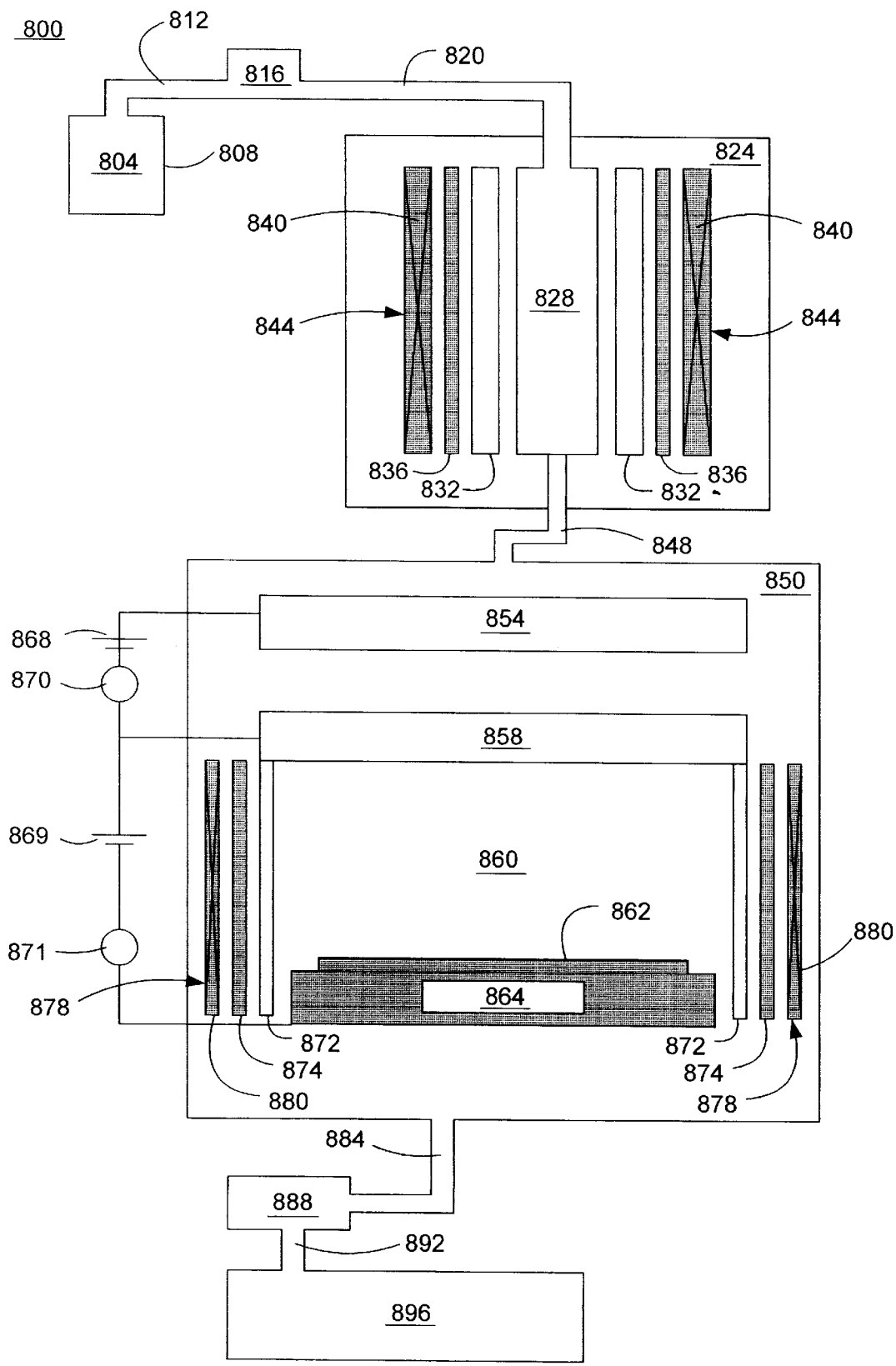
FIG. 21 depicts a combined transport polymerizatiotn and chemical vapor deposition apparatus utilizing combined photon and plasma processes.

A high density plasma deposition process can also be used to dissociate precursors. In contrast to the low density plasma process described above, in high density plasmas, the electron density is in the range of from about $10^{13}$ to $10^{15}$ electrons/$cm^3$. This process must be carried at lower pressures than conventional plasma processes. In this embodiment, a inductively coupled high density plasma apparatus 700 is shown schematically in FIG. 20. A precursor delivery system 704 volatilizes or vaporizes the precursor, which flows through a pipe 708 and an anode gas injector 712 into the deposition chamber 716. The anode gas injector 712 is attached to RF generators 720 which are matched by matching controllers 724. The output of the RF generators 720 passes through inductive coils 728 to produce an electrical field. The wafer 732 is held by a cathode electrostatic chuck 736, which is connected to the RF generator 720. IR, UV, and VUV sources 740 provide additional heating of precursors to decrease the needed plasma power. The plasma source power is in the range of about 1 Watts/$cm^2$ of wafer surface area to about 15 Watts/$cm^2$, preferably about 2 Watts/$cm^2$ to about 10 Watts/$cm^2$ and more preferably about 5 Watts/$cm^2$. The chamber pressure is maintained in the range of 0.01 milliTorr to 10 milliTorr, and preferably below 5 milliTorr by a pump and cold trap (not shown). The wafer temperature is in the range from about 300° C. to 450° C., and is preferably about 350° C.

d. Combined Transport Polymerization and CVD Apparatus Utilizing Combined Photon and Plasma Processes FIG. 21 depicts a schematic diagram of a TP and CVD reactor 800 embodying the elements for photon-plasma and IR dissociation and deposition. Precursors 804 are stored in a precursor container 808 which is connected via a pipe 812 to a mass flow controller 816. For TP, precursors are transported into a dissociation reactor 824 which houses the dissociation chamber 828. The wall of reactor 824 is made of crystalline materials such as LiF, $MgF_2$, or $CaF_2$, which permits light of vacuum ultraviolet wavelengths to pass. Vacuum ultraviolet and ultraviolet light is generated by a silent discharge plasma generators 832, which are place inside infrared heaters 836. The infrared heaters 836 are placed inside DC magnets 840 and AC magnets 844. The magnets regulate the flow of plasma during dissociation, and the reactive intermediates so generated are transported to a deposition reactor 850.

The deposition reactor 850 contains a deposition chamber 860 containing a gas and reactant dispersion manifold 854, a gas and reactant dispersion plate 858. The walls of the deposition chamber are made of crystalline materials such as LiF, $MgF_2$, or $CaF_2$, which permits light of vacuum ultraviolet wavelengths to pass. The gas dispersion manifold 854 and the gas dispersion plate 858, are used to adjust the distribution and homogeneity of the intermediates. The intermediates are directed toward the wafer 862, which is held on a cold chuck 864. The gas dispersion manifold 854 and dispersion plate 858 are connected in parallel to a DC voltage bias anode 868, a DC voltage bias cathode 869, an AC voltage bias anode 870, and an AC voltage bias cathode 871. Silent discharge plasma generators 872 are placed outside the deposition chamber 860. Infrared heaters 874 are placed outside the silent plasma discharge generators 860 and DC magnets 878 and AC magnets 880 are placed outside the infrared heaters 874. Gases exit the deposition chamber 860 through a pipe 884, pass through a cold or reactive trap 888, pass through another pipe 892 to a vacuum pump 896. The pressure in the systems is maintained at a desired pressure using pump 896. The trap 888 protects the pump from deposition of intermediates.

For CVD, the deposition chamber can be used without the dissociation reactor. Precursors are placed directly on wafer 862. and the chuck 864 is not cooled. IR, UV, or VUV radiation is directed toward the wafer 862. The radiation dissociates the precursor, and deposition of intermediates and polymerization takes place on the wafer.

Table 4 shows process conditions for combined photon-plasma assisted precursor dissociation using chamber 828, and Table 5 shows process conditions for combined photon-plasma precursor deposition in deposition chamber 860.

TABLE 4

Process Conditions for Photon-Plasma Precursor Dissociation

| Variable | Range | Preferred Range |
|---|---|---|
| Temperature | 200° C.–600° C. | 350° C.–500° C. |
| Photon Wavelength | 100 nm–400 nm | 140 nm–300 nm |
| Photon Energy | 2.5 eV–12 eV | 4 eV–9 eV |
| Photon Flux | 10 milliW/$cm^2$–5 W/$cm^2$ | 40–100 milliW/$cm^2$ |
| Plasma Density | $10^{12}$–$10^{14}$ electrons/$cm^3$ | $10^{13}$ electrons/$cm^3$ |
| Pressure | 0.1 milliTorr–10 Torr | 1 milliTorr–100 milliTorr |

TABLE 5

Process Conditions for Photon-Plasma Precursor Deposition

| Variable | Range | Preferred Range |
|---|---|---|
| Temperature | −20° C.–300° C. | −100° C. |
| Photon Wavelength | 100 nm–400 nm | 250 nm |
| Photon Energy | 2.5 eV–12 eV | 4.5 eV |
| Photon Flux | 10 milliW/$cm^2$–5 W/$cm^2$ | 10–100 milliW/$cm^2$ |
| Plasma Density | $10^{12}$–$10^{14}$ electrons/$cm^3$ | $10^{13}$ electrons/$cm^3$ |
| Pressure | 0.1 milliTorr–10 Torr | 1 milliTorr–100 milliTorr |

Table 6 shows the process conditions used for chemical vapor deposition using apparatus of this invention without a separate dissociation chamber.

TABLE 6

Process Conditions for Chemical Vapor Deposition

| Variable | Range | Preferred Range |
|---|---|---|
| DC Bias Voltage | 100–2000 V | 500 V |
| AC Bias Voltage | 10–200 V | 50 V |
| Pulsed Bias Voltage | 100–4000 V | 500 V |

TABLE 6-continued

Process Conditions for Chemical Vapor Deposition

| Variable | Range | Preferred Range |
|---|---|---|
| Pulse Width | 10–1000 msec | 1 msec |
| Pulse Frequency | 10 Hz–1000 Hz | 60 Hz |
| DC Magnetic Field Strength | 100–2000 Gauss | 700 Gauss |
| AC Magnetic Field Strength | 100–1000 Gauss | 500 Gauss |
| AC frequency | 10 Hz–500 Hz | 50 Hz–60 Hz |
| Pressure in Silent Discharge Generator | 100 Torr–1500 Torr | 760 Torr |
| AC Power to Silent Discharge Generator | 100 Watts–2000 Watts | 500 Watts |

The plasma density is reported as electron density, but it is to be noted that ion density must be the same to maintain charge neutrality of the plasma. Any non-uniformity of charge distribution can result in plasma damage to the thin film of low dielectric material, as well as imparting charge to the integrated circuit components.

Control of the plasma is by a magnetic field within the precursor chamber and in the deposition chamber. In the precursor reactor, the plasma is confined to any desired area, such as the center of the reactor. Additionally, alternating the polarity of the magnetic field stirs the plasma, ensuring even energy distribution within the plasma, thereby increasing the efficiency of dissociation of precursor molecules into reactive intermediates. In the deposition chamber, the magnetic field is used to control the pattern of distribution of intermediates over the wafer. This would serve two purposes: (1) to direct the deposition of precursor to the desired portion of the surface, thus conserving the precursor, and (2) minimize film deposition on other parts of the reactor chamber, thus minimizing the required cleaning, minimizing particle generation, and simplifying the reactor chamber design.

Another feature comprises the placement of an electrical bias voltage within the deposition chamber. This provides a further means of controlling the flow of plasma-ionized species to the site of deposition on the wafer. A bias voltage, in the form of direct current (DC) or alternating current (AC) can be applied and modulated. Pulsed voltages can be used to alter the flow pattern of ions to either accelerate, decelerate, or to regulate the density of the plasma ions in the stream reaching the wafer. Optimization of ion velocity and flow thus can be obtained using various combinations of magnetic field and bias voltage. Table 7 shows the ranges of the various magnetic field and bias voltage variables which are regulated in the dissociation portion of this invention.

TABLE 7

Optimization of Electrical and Magnetic Field Variables for Dissociation

| Variable | Range | Preferred Range |
|---|---|---|
| Pressure in Silent Discharge Generator | 100 Torr–1500 Torr | 500 Torr |
| AC Power to Silent Discharge Generator | 100 Watts–2000 Watts | 500 Watts |
| AC Magnetic Field Strength | 100 Gauss–1000 Gauss | 500 Gauss |
| DC Magnetic Field Strength | 100 Gauss–2000 Gauss | 700 Gauss |

Table 8 shows process conditions which can be used to optimize deposition of polymers.

TABLE 8

Optimization of Electrical and Magnetic Field Variables for Deposition

| Variable | Range | Preferred Range |
|---|---|---|
| DC Bias Voltage | 100–2000 V | 500 V |
| AC Bias Voltage | 10–200 V | 50 V |
| Pulsed Bias Voltage | 100–4000 V | 500 V |
| Pulse Width | 10–1000 msec | 1 msec |
| Pulse Frequency | 10 Hz–1000 Hz | 60 Hz |
| DC Magnetic Field Strength | 100–2000 Gauss | 700 Gauss |
| AC Magnetic Field Strength | 100–1000 Gauss | 500 Gauss |
| AC frequency | 10 Hz–500 Hz | 50 Hz–60 Hz |

Other reactors and reactor configurations may be used, as exemplified by co-pending applications.

VI. Manufacture of Integrated Circuit Chips

The above precursors and methods are intended to provide polymers with low dielectric constants and high thermal stability for the manufacture of integrated circuits. FIG. 22 depicts a diagram of a multi-level integrated circuit chip 900 embodying the features of this invention. The substrate 904 is planarized prior to further processing. Then a source region 908, a drain region 912, and a polysilicon gate 916 are manufactured on the substrate 904. The wafer 900 is inserted into a deposition chamber for TP or CVD, and a first Interlevel dielectric (ILD) layer 920 of linear polymer or cross-linked polymer. overlays the substrate 904 and polysilicate gate 916. A floating polysilicon gate 924 is overlain by a second ILD layer 928, a first metal line 932 and an intermetal dielectric (IMD) layer 936. On top of the IMD layer 936, a second metal line 940 and a second IMD layer 944 is deposited. After each step of the deposition is completed, the wafer can planarized using chemical mechanical polishing or other method known in the art.

The polymer surface is subjected to chemical mechanical planarization to create a smooth, flat, and defined surface for further layers of polymer and metal. After a second layer of metal interconnect lines is deposited on the planarized surface, the wafer is inserted into a CVD chamber, wherein a second layer of polymer is deposited, again, filling the gaps between the metal lines. After a second chemical mechanical planarization process, the wafer is completed and additional layers can be deposited through repetition of the processes just described.

A. Manufacture of Integrated Circuit Chips Made Combinations of Different Polymers By varying the composition of different precursors, different polymer properties can be attained. For example, by combining di-functional precursors with multi-functional precursors, it is possible to manufacture polymers with properties different from those of either precursor alone. Because the multi-functional precursors can form cross-links with other polymers, the resulting thin film will have increased mechanical strength. By diluting the multi-functional precursor with di-functional precursor, the mechanical strength of the thin film can be tailored to suit the individual needs of the user.

Moreover, by varying the composition of precursors during the TP or CVD processes it is possible to vary the composition of the polymer layer during its deposition. Thus, a user may deposit one type of polymer close to the substrate and change the composition of the polymer progressively, resulting in a different polymer at the surface of the dielectric layer. Such changes in polymer composition can be done step-wise by ceasing delivery of a first precursor and starting the delivery of a second precursor. Moreover, subsequent different layers of polymer may be deposited by changing to third and subsequent precursors. Furthermore, a gradient in polymer composition is achieved by gradually changing the relative proportions of different precursors during deposition.

VII. General Methods for Measuring Properties of Polymer Thin Films

The dielectric constant, K, is measured by fabricating a capacitor and measuring the capacitance over a range of frequencies. From the capacitor dimensions and film thickness, the K is then calculated using methods known in the art. Alternatively, the dielectric constant K of polymer thin films is determined by measuring the refractive index of the deposited film using methods known in the art. The K is then calculated as the square of the refractive index.

The glass transition temperature Tg can be determined from observing changes in heat capacity, modulus, or thermal expansion of a polymer specimen with changes in temperature. For example, Tg can be obtained by heating a polymer specimen in a differential scanning calorimeter (DSC) that measures the heat capacity of the polymer or by a thermal mechanical analyzer (TMA) that measures thermal expansion of the polymer as the temperature is increased. These methods are standard in the art and will not be discussed further.

The thermal stability is reflected by the decomposition temperature (Td) of a polymer. The Td is determined using a thermogravimetric analyzer (TGA). The wafer is progressively heated, and the weight loss of the sample is determined using a microbalance. Commonly, this is done in a nitrogen atmosphere to eliminate the possibility of oxidation of the polymers during heating. Published data such as the % weight loss and initial weight loss temperature, shows that Td depends not only on the temperature, but also upon the heating rate employed during measurements. This method is standard in the art and will not be discussed further.

Elastic modulus E, and shear modulus, G, are obtained using well known ASTM methods, which will not be discussed further. The residual stress on a polymer on a Si substrate, $\sigma^r$, can be assessed using a bending beam method (BBM) that monitors polymer/Si beam deflections resulting from mismatch of the coefficients of thermal expansion (CTE) of the polymer thin film and the Si substrate. Therefore, the deflections caused by a beam directed at a polymer/Si substrate sample relative to the deflections of a beam directed on the Si substrate sample are recorded over various temperatures prior to deposition. From this information, the residual stress can be calculated using standard methods, which will not be discussed further.

Other embodiments of the invention are described in the Examples below.

EXAMPLES

Example 1

Relationship Between Polymer Structure and Decomposition Temperature (Td)

Figure 23:
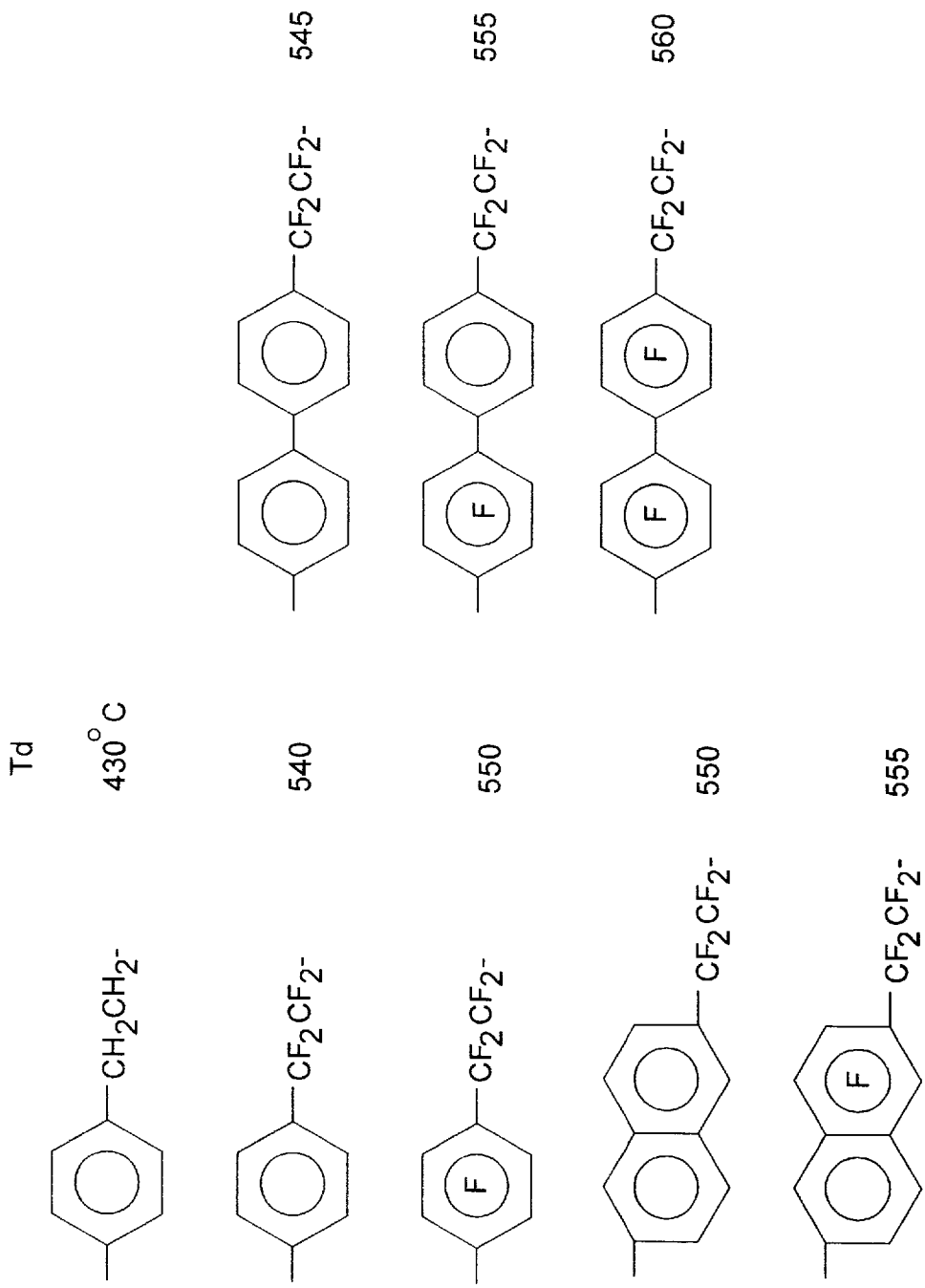
FIG. 23 depicts the relationship between polymer structure and decomposition temperature (Td) for polymers comprising selected aromatic moieties.

FIG. 23 shows the relationship between polymer structure and calculated decomposition temperature (Td) expressed in degrees C. Calculations were made according to methods of Lee et al., *Rev. Macromol. Chem. Phys.* C29(4):431–569 (1989), Lee et al., *Polym. Eng & Sci.* 27(13): 1015–1017 (1987), and Bicerano, *Prediction of Polymer Properties*, Marcel Dekker, New York (1996), herein incorporated fully by reference. Compared to —$C_4H_4$—$CH_2$—$CH_2$, which had a Td of 430° C., fully fluorinating the methylene groups increased Td to 540° C. Further, by completely fluorinating the phenylenyl group, Td increased to 550° C. The polymer containing a di-phenylenyl moiety and two fluorinated methylene moieties (—$C_4H_4$—$C_4H_4$—$CF_2$—$CF_2$), had a Td of 545° C. Completely fluorinating one ring of the di-phenylenyl moiety increased Td to 555° C., and completely fluorinating both rings of the di-phenylenyl moiety increased Td to 560° C. Compared to $C_4H_4$—$CF_2$—$CF_2$, replacing the phenylenyl moiety with a naphthalenyl moiety (—$C_{10}H_6$—) increased Td from 540° C. to 550° C., and completely fluorinating one ring of the naphthalenyl moiety further increased Td to 555° C. Thus, increasing the number of fluorine atoms in polymers increases the Td. By increasing the number of possible fluorination sites on the aromatic ring structure, it is possible to increase Td.

Example 2

Relationship Between Polymer Structure and Glass Transition Temperature (Tg)

Figure 24:
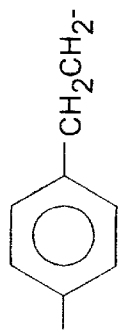
FIG. 24 depicts the relationship between polymer structure and glass transition temperature (Tg) for polymers comprising selected aromatic moieties.

FIG. 24 shows the relationship between polymer structure, polymer fluorination and calculated Tg. Compared to $CH_2$—$CH_2$—, which had a Tg of −75° C., adding a phenylenyl moiety (thus making: —$C_6H_4$—$CH_2$—$CH_2$), increased Tg to 58° C. Further, fully fluorinating the methylene groups increased Tg to 172° C. Moreover, by completely fluorinating the phenylenyl moiety, Tg increased to 301° C. The polymer containing a di-phenylenyl moiety and two fluorinated methylene moieties (—$C_6H_4$—$C_6H_4$—$CF_2$—$CF_2$), had a Tg of 211° C., completely fluorinating one ring of the di-phenylenyl moiety increased Tg to 300° C., nearly the same as the structure with only one phenylenyl moiety. Furthermore, completely fluorinating both rings of the di-phenylenyl moiety increased Tg to 394° C. Compared to $C_6H_4$—$CF_2$—$CF_2$, replacing the phenylenyl moiety with a naphthalenyl moiety (—$C_{10}H_6$—) increased Tg from 172° C. to 200° C., and completely fluorinating one ring of the naphthalenyl moiety further increases Tg to 346° C. Thus, increasing the number of fluorine atoms in polymers increases the Td. By increasing the number of possible fluorination sites on the aromatic ring structure, it is possible to increase Tg.

Example 3

Relationship Between Polymer Structure and Elastic Modulus (E)

Figure 25:
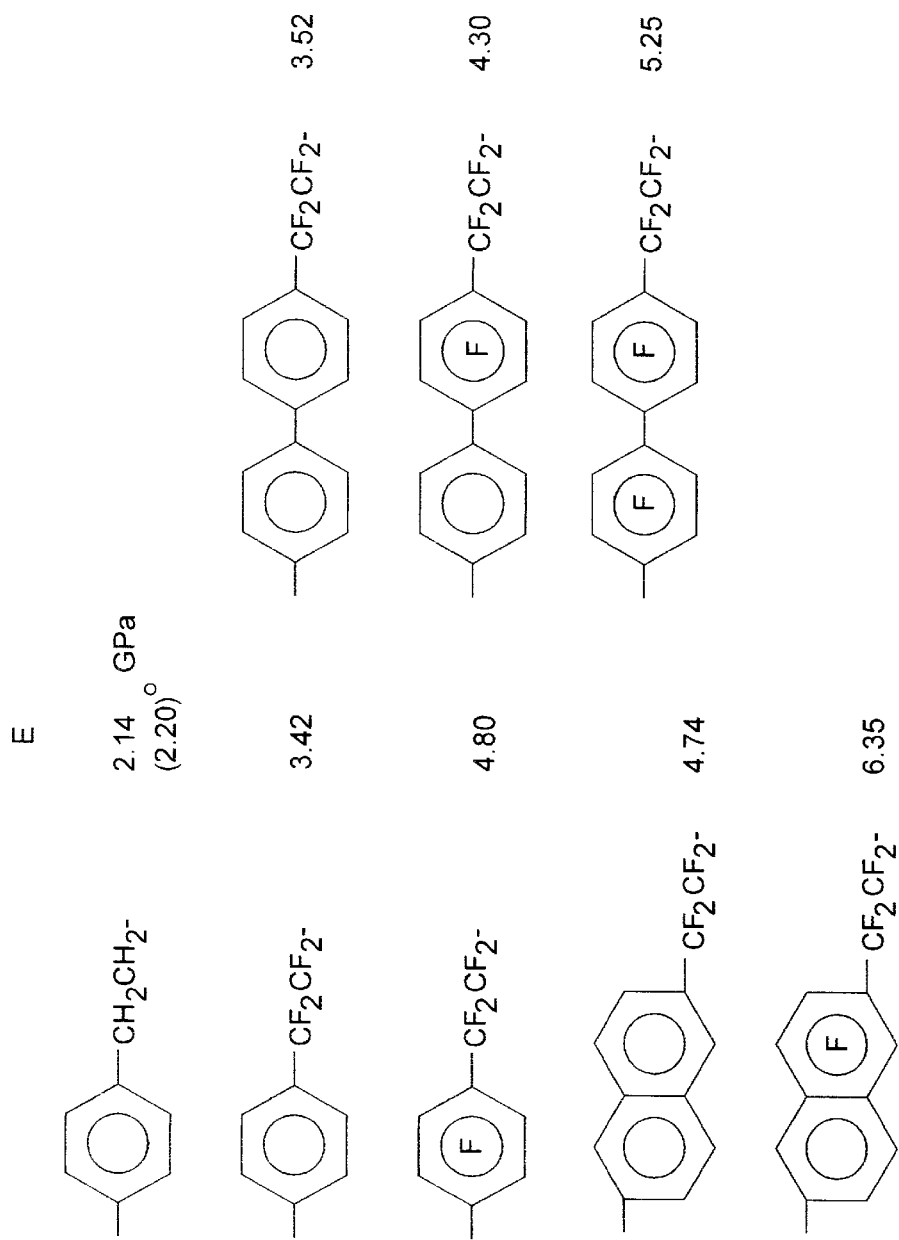
FIG. 25 depicts the relationship between polymer structure and elastic modulus (E) for polymers comprising selected aromatic moieties.

FIG. 25 shows the relationship between polymer structure, polymer fluorination and the calculated Elastic Modulus (E), expressed in gigaPascals (GPa). Compared to —$C_6H_4$—$CH_2$—$CH_2$, which had an E of 2.14, fully fluorinating the methylene groups increased E to 3.42. Moreover, by completely fluorinating the phenylenyl group, E increased to 4.80. The polymer containing a di-phenylenyl moiety and two fluorinated methylene moieties (—$C_6H_4$—$C_6H_4$—$CF_2$—$CF_2$), had an E of 3.52. Completely fluorinating one ring of the di-phenylenyl moiety increased E to 4.30. Furthermore, completely fluorinating both rings of the di-phenylenyl moiety increased E to 5.25. Compared to $C_6H_4$—$CF_2$—$CF_2$, replacing the phenylenyl moiety with a naphthalenyl moiety (—$C_{10}H_6$—) increased E from 3.42 to 4.74, and completely fluorinating one ring of the napthalenyl moiety further increased E to 6.35. Thus, increasing the number of fluorine atoms in polymers increases the E. By increasing the number of possible fluorination sites on the aromatic ring structure, it is possible to increase E Example 4

Relationship Between Polymer Structure and Shear Modulus (G)

Figure 26:
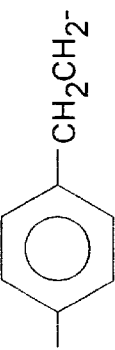
FIG. 26 depicts the relationship between polymer structure and shear modulus (G) for polymers comprising selected aromatic moieties.

FIG. 26 shows the relationship between polymer structure, polymer fluorination and calculated shear modulus (G), expressed in gigaPascals (GPa). Compared to —$C_6H_4$—$CH_2$—$CH_2$, which had a G of 0.29, fully fluorinating the methylene groups increased E to 0.35. Moreover, by completely fluorinating the phenylenyl group, G increased to 0.42. The polymer containing a di-phenylenyl moiety and two fluorinated methylene moieties (—$C_6H_4$—$C_6H_4$—$CF_2$—$CF_2$), had a G of 0.34 and completely fluorinating one ring of the di-phenylenyl moiety increased G to 0.38. Furthermore, completely fluorinating both rings of the di-phenylenyl moiety increased G to 0.42. Compared to $C_6H_4$—$CF_2$—$CF_2$, replacing the phenylenyl moiety with a naphthalenyl moiety (—$C_{10}H_6$—) increased G from 0.35 to 0.5, and completely fluorinating one ring of the naphthalenyl moiety further increased G to 0.57. Thus, increasing the number of fluorine atoms in polymers increases G. By increasing the number of possible fluorination sites on the aromatic ring structure, it is possible to further increase G.

Example 5

Relationship Between Polymer Structure and Dielectric Constant (K)

Figure 27:
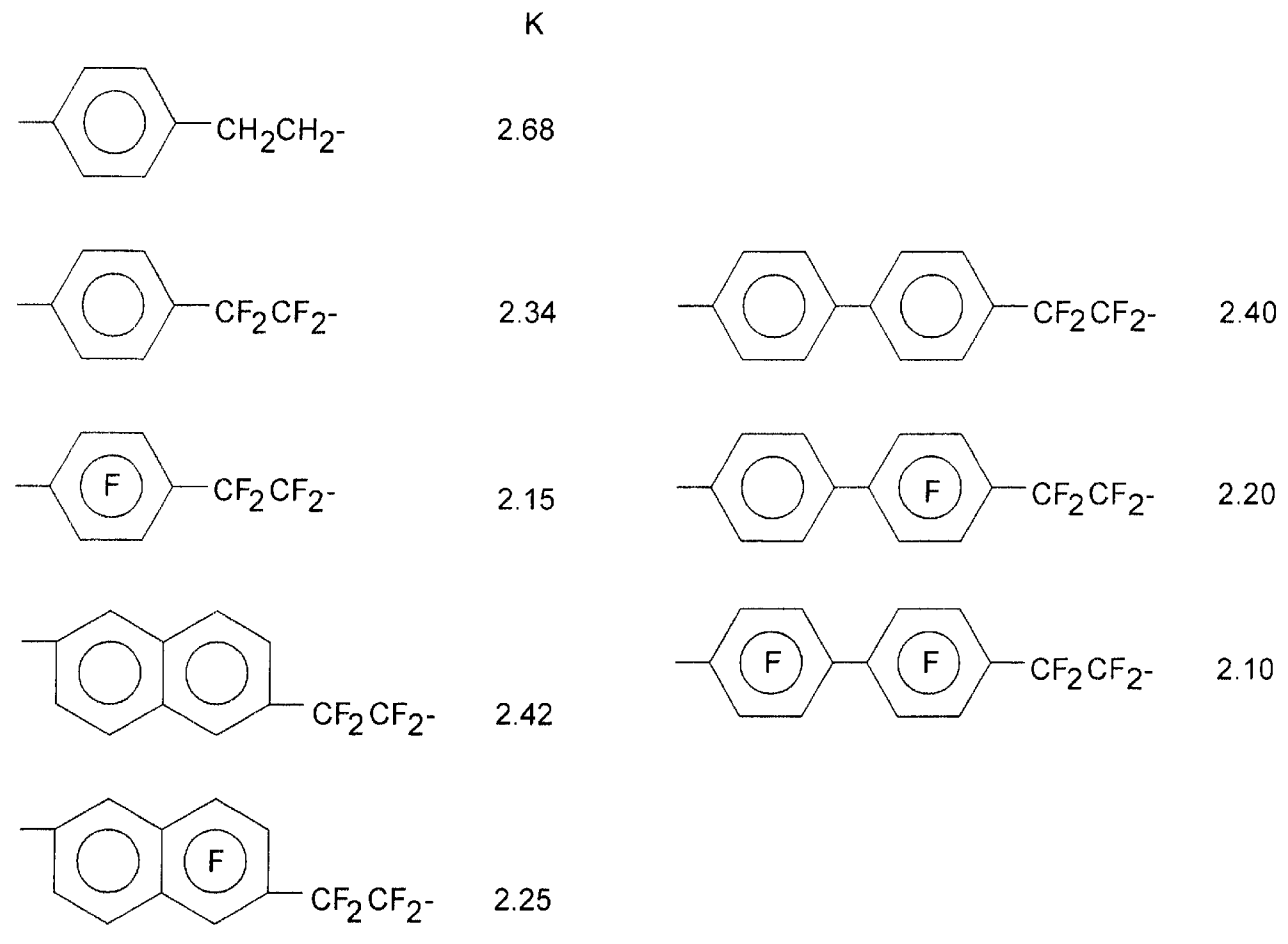

FIG. 27 shows the relationship between polymer structure, polymer fluorination and the calculated dielectric constant (K). Compared to —$C_6H_4$—$CH_2$—$CH_2$, which had a K of 2.68, fully fluorinating the methylene groups decreased K to 2.34. Moreover, by completely fluorinating the phenylenyl group, K decreased further to 2.15. The polymer containing a di-phenylenyl moiety and two fluorinated methylene moieties (—$C_6H_4$—$C_6H_4$—$CF_2$—$CF_2$), had a K of 2.40. Completely fluorinating one ring of the di-phenylenyl moiety decreased K to 2.20. Furthermore, completely fluorinating both rings of the di-phenylenyl moiety decreased K to 2.10. Compared to $C_6H_4$—$CF_2$—$CF_2$, replacing the phenylenyl moiety with a naphthalenyl moiety (—$C_{10}H_6$—) increased K from 2.34 to 2.42, but completely fluorinating one ring of the naphthalenyl moiety decreased K to 2.25. Thus, increasing the number of fluorine atoms in polymers decreases K. By increasing the number of possible fluorination sites on the aromatic ring structure, it is possible to further decrease K.

Example 6

Summary of Polymer Structure and Dielectric and Physical Properties of Selected Aromatic Moieties FIG. 28 shows a summary of some of the effects of polymer structure on calculated values of dielectric constant (K). decomposition temperature (Td) measured in nitrogen atmosphere and expressed in degrees C. glass transition temperature (Tg) expressed in degrees C. elastic modulus (E) expressed in gigaPascals (GPa), and shear modulus (G) expressed in gigaPascals (GPa). Increasing the number of $sp^2$ C-$sp^2$ C bonds by increasing the size or number of aromatic residues in the polymer decreases K, and increases Td, Tg, E, and G. The effect of rigidly joining two rings together (comparing di-phenylenyl moiety with the naphthalenyl moiety) slightly increased K (from 2.40 to 2.42) and slightly increased Td (from 545° C. to 550° C., increased E (from 3.52 to 4.73). increased G (from 0.34 to 0.50)? but decreased Tg (from 211° C. to 200° C.).

Moreover, for each type of aromatic moiety, increasing the number of fluorine atoms in the aromatic ring decreased K, and increased Td, Tg, E, and G.

The foregoing descriptions and Examples are included for illustrative purposes only, and are not intended to limit the scope of the invention. Other features, aspects and objects of the invention can be obtained from a review of the figures and the claims. It is to be understood that other embodiments of the invention can be developed and fall within the spirit and scope of the invention and claims.

Incorporation of Reference

Each of the references cited above in this application is herein incorporated fully, by reference.

Industrial Applicability

This invention includes novel precursors and methods for making polymers with low dielectric constant high thermal stability and high mechanical strength. The polymers include fluorinated aromatic moieties and can be used to manufacture thin films which are applicable, as for example, for integrated circuits, electronic and optical device interconnect and micromechanical devices.

What is claimed is:

1. A polymer comprising —$(CF_2$—Ar—$CF_2$—$)_n$, wherein n is an integer of at least 20, and wherein Ar is an aromatic moiety of more than 6 carbon atoms and less than about 40 aromatic carbon atoms.

2. The polymer of claim 1, wherein a unit of said polymer has a ratio of $sp^2C/sp^3C$ bonds from about 3 to about 20, and wherein $sp^3C$ bonds include $sp^2C$—$sp^3C$ bonds and $sp^3C$—$sp^3C$ bonds, and wherein $sp^2C$ bonds include $sp^2C$—$sp^2C$ bonds.

3. The polymer of claim 1, wherein a fluorine atom is bonded to a carbon atom in the aromatic moiety by a $sp^2C$—F bond.

4. The polymer of claim 1, wherein a unit of said polymer has a $sp^2C$—H/$sp^3C$—H bond ratio in the range of about 3 to about 6.

5. The polymer of claim 1, wherein when the $sp^2C$—H/$sp^3C$—H bond ratio is at least 3, and the aromatic moiety has $sp^2C$—F bonded fluorine atoms in the range of from 1 to the maximum allowable for the aromatic moiety.

6. The polymer of claim 1, 3, or 5 wherein the dielectric constant is less than about 2.6, glass transition temperature is greater than about 100° C. and wherein the weight loss is less than about 0.8%/hr under nitrogen atmosphere for 3 hours at about 350° C.

7. The polymer of claim 1, 3, or 5 wherein the dielectric constant is less than about 2.3.

8. The polymer of claim 1, 3, or 5 wherein the dielectric constant is less than about 2.0.

9. The polymer of claim 1, 3, or 5 wherein the glass transition temperature is greater than about 200° C.

10. The polymer of claim 1, 3, or 5 wherein the glass transition temperature is greater than about 250° C.

11. The polymer of claim 1, 3, or 5 wherein the glass transition temperature is greater than about 300° C.

12. The polymer of claim 1, 3, or 5 wherein the glass transition temperature is greater than about 350° C.

13. The polymer of claim 1, 3, or 5 wherein the glass transition temperature is about 400° C.

14. The polymer of claim 1, 3, or 5 wherein the weight loss is less than about 0.8%/hr under nitrogen atmosphere for 3 hours at about 400° C.

15. A polymer for a semiconductor wafer comprising the structure —$CH_oF_{2-o}$—Ar—$CH_pF_{2-p}$—, wherein o and p are integers of 0, 1 or 2 and wherein Ar is an aromatic moiety of greater than 6 and less than about 40 carbon atoms, said moiety containing at least one fluorine atom.

16. A polymer for a semiconductor wafer comprising the structure —$CH_oF_{2-o}$—Ar—$CH_pF_{2-p}$—, wherein o and p are integers of 0, 1 or 2 and wherein Ar is an aromatic moiety of greater than 6 to about 40 carbon atoms, said aromatic moiety being fully fluorinated.

17. A polymer for a semiconductor wafer comprising the structure —$CH_oF_{2-o}$—Ar—$CH_pF_{2-p}$—, wherein o and p are integers of 0, 1 or 2 and wherein Ar is an aromatic moiety of greater than 6 to about 40 carbon atoms, said aromatic moiety containing at least one $sp^2C$—F bond.

18. A polymer comprising an aromatic moiety having between about 6 and about 40 carbon atoms and having at least one fluorine atom having an $sp^2C$—F bond, said polymer having a dielectric constant between about 2.0 and about 2.6, a Td between about 250° C. and about 565° C., a Tg between about 150° C. and about 450° C., an E between about 4 and about 10 GPa, and a G between about 0.4 and about 2 GPa.

19. The polymer of claim 1, wherein the aromatic moiety has an end-to-end length and is symmetrical about an axis defined by the end-to-end length.

20. A method for making a polymer having the structure —$CH_oF_{2-o}$—Ar—$CH_pF_{2-p}$—, wherein o and p are integers of 0, 1 or 2 and wherein Ar is an aromatic moiety containing from greater than 6 and about 40 carbon atoms and having at least one property selected from the group consisting of decreasing the dielectric constant and increasing one of the Td, Tg, E, or G, said method comprising selecting an aromatic moiety having at least one fluorine atom having an $sp^2C$—F bond.

21. The polymer of claim 1 comprising an aromatic moiety having the following formula: $C_{12}H_{(8-n)}F_n$, wherein n is an integer ranging from 0 to 8.

22. The polymer of claim 1 wherein Ar is $C_{12}F_8$.

* * * * *

UNITED STATES PATENT AND TRADEMARK OFFICE
CERTIFICATE OF CORRECTION

PATENT NO.      : 6,323,297 B1
DATED           : November 27, 2001
INVENTOR(S)     : Chung J. Lee, Hui Wang and Giovanni Antonio Foggiato It is certified that error appears in the above-identified patent and that said Letters Patent is hereby corrected as shown below:

Title page,
Item [56], References Cited, please add the following references:

Kudo, et al., Characteristics of Plasma-CF Films for Very Low-K Dilelectrics, February 10-11, 1997, DUMIC Conference, 1997 ISMIC_ 222D/97/0034, 85-92.

Labelle, et al., Characterization of Pulsed-Plasma Enhanced Chemical Vapor Deposited Fluorocarbon Thin Films, February 10-11, 1997, DUMIC Conference, 1997 ISMIC- 222D/97/0034, 98-105.

Lang, et al., Vapor Deposition of Very Low K Polymer Films, Poly(Naphthalene), Poly (Flourinated Naphthalene), Mat. Res. Soc. Symp. Proc., Vol. 381, 45-50, 1995.

Lee, Correlations of Elastic Modulus, Cohesive Energy Density and Heat Capacity Jump of Glassy Polymers, Polymer Engineering and Science, Vol. 27, No. 13, 1015-1017, July 1987.

Lee, Polyimides, Polyquinolines and Polyquinoxalines: Tg-Structure Relationships, JMS-Rev. Macromol. Chem. Phys., C29(4), 431-460, 1989.

Lee, Transport Polymerization of Gaseous Intermediates and Polymer Crystals Growth, J. Macromol. Sci.-Rev. Macromol. Chem., C16(1), 79-127, 1977-1978.

J.I. Krochiwitz, Encyclopedia of Chem. Tech., Vol. 5, 320-373, 1991.

Meriaudeau, et al., Dehydrocyclization of Alkanes Over Zeolite-Supported Metal Catalysts: Monofunctional or Bifunctional Route, Catal. Rev.-Sci. Eng., 29(1&2), 5-48, 1997.

J.J. McKetta, Encyclopedia of Chem. Proc. & Design, Vol. 14, 276-291, 1992.

Selbrede, S., et al., Characterization of Parylene-N-Thin Films for Low Dielectric Constant VLSI Applications, February 10-11, 1997, DUMIC Conference, 1997 ISMIC - 222D/97/0034, 121-124.

Sharangpani, et al., Advantages of Chemical Vapor Deposition Over Conventional Techniques for the Processing of Amorphous Teflon Fluoropolymer, February 10-11, 1997, DUMIC Conference, 1997 ISMIC - 222D/97/0034, 117-120.

UNITED STATES PATENT AND TRADEMARK OFFICE
CERTIFICATE OF CORRECTION

| | |
|---|---|
| PATENT NO. | : 6,323,297 B1 |
| DATED | : November 27, 2001 |
| INVENTOR(S) | : Chung J. Lee, Hui Wang and Giovanni Antonio Foggiato |

It is certified that error appears in the above-identified patent and that said Letters Patent is hereby corrected as shown below:

Item [56], References Cited, please add the following references:

Singer, 1997: The Dawn of Quarter Micron Production, Semiconductor International, January 1997, 50-56.

Wang, et al., Parylene-N Thermal Stability Increase by Oxygen Reduction-Low Substrate Temperature Deposition, Preannealing, and PETEOS Encapsulation, February 10-11, 1997, DUMIC Conference, 1997 ISMIC - 222D/97/0034, 125-128

Wary, et al., Polymer Developed to be Interlayer Dielectric, Semi-Conductor International, 211-216, June 1996.

Josef Bicerano, Prediction of Polymer Properties, Second Edition, Marcel Dekker, Inc.. pp. 1-15, 50-61, 108-111, and 280-295.

U.S. PATENT DOCUMENTS, please list the following:

3,440,277 April 22, 1969 Holland, et al.
4,291,244 Sept. 22, 1981 Beach, et al.
5,139,813 Aug. 18, 1992 Yira, et al.
5,210,341 May 11, 1993 Dolbier, Jr., et al.
5,334,454 Feb. 8, 1994 Caporiccio, et al.
5,324,813 Jun. 28, 1994 Hougham, et al.
5,424,097 Jun. 13, 1995 Olson, et al.
5,534,068 Jul. 9, 1996 Beach, et al.
5,536,317 Jul. 16, 1996 Crain, et al.
5,536,892 Jul. 16, 1996 Dolbier, Jr., et al.
5,536,321 Jul. 16, 1996 Olsen, et al.
5,536,319 Jul. 16, 1996 Wary, et al.
5,536,322 Jul. 16, 1996 Wary, et al.
5,783,614 Jul 21, 1998 Chen, et al.
5,538,758 Jul. 23, 1996 Beach, et al.
5,556,473 Sept. 17, 1996 Olson, et al.
5,637,395 Jun. 10, 1997 Uemura, et al.
3,268,599 Aug. 23, 1966 Chow, et al.
3,342,754 Sep. 19, 1967 Gorham
5,268,202 Dec. 7, 1993 You, et al.

UNITED STATES PATENT AND TRADEMARK OFFICE
CERTIFICATE OF CORRECTION

PATENT NO. : 6,323,297 B1
DATED : November 27, 2001
INVENTOR(S) : Chung J. Lee, Hui Wang and Giovanni Antonio Foggiato It is certified that error appears in the above-identified patent and that said Letters Patent is hereby corrected as shown below:

FOREIGN PATENT DOCUMENTS, please list the following:

| | | | |
|---|---|---|---|
| WO | 98/24743 | 11 June 1998 | PCT |
| WO | 97/15699 | 01 May 1997 | PCT |
| WO | 97/15951 | 01 May 1997 | PCT |
| WO | 97/14666 | 24 April 1997 | PCT |
| WO | 98/41490 | 24 Sept. 1998 | PCT |
| EP 0 769 788 A2 | | 23 April 1997 | EP |
| JP 60,231,442 | | 18 Nov. 1985 | JP |
| EP, A, 900, 722 | | 10 March 1999 | EP |

OTHER DOCUMENTS, please list the following:

Hosakawa, et al., Synthesis of bis(trifluoromethyl)naphthalenes, Chemical Abstract, 1987, CA 87: 167788
Malysheva, et al., Reaction of octafluoronaphthalene with potassium fluoride and Ftoroplast 4, Chemical Abstract, 1974, CA 81: 91237
Okamoto, et al., Orbital unsymmertrization affects facial selectivities of Diels-Alder dienophiles, J. Org. Chem., 1996 Vol. 61, pages 3155-3166.
Bennett, et al., Insertion reactions of benzene-nickel (0) complexes with acetylenes, Chemical Abstract, 1995, CA 122:187777.
Okano, et al., Synthesis and polymerization of some ethynyl(trifluoromethyl) naphathalenes, Chemical Abstract, 1995, CA 122: 186690.

Signed and Sealed this

Nineteenth Day of November, 2002

*Attest:*

*Attesting Officer*

JAMES E. ROGAN
*Director of the United States Patent and Trademark Office*